(12) United States Patent
Silver

(10) Patent No.: US 12,357,628 B2
(45) Date of Patent: Jul. 15, 2025

(54) PREVENTION AND TREATMENT OF ORGAN FIBROSIS

(71) Applicant: CORNELL UNIVERSITY, Ithaca, NY (US)

(72) Inventor: Randi Silver, Ithaca, NY (US)

(73) Assignee: Cornell University, Ithaca, NY (US)

(*) Notice: Subject to any disclaimer, the term of this patent is extended or adjusted under 35 U.S.C. 154(b) by 1306 days.

(21) Appl. No.: 16/961,066

(22) PCT Filed: Jan. 9, 2019

(86) PCT No.: PCT/US2019/012856
§ 371 (c)(1),
(2) Date: Jul. 9, 2020

(87) PCT Pub. No.: WO2019/139956
PCT Pub. Date: Jul. 18, 2019

(65) Prior Publication Data
US 2020/0397777 A1    Dec. 24, 2020

Related U.S. Application Data

(60) Provisional application No. 62/699,424, filed on Jul. 17, 2018, provisional application No. 62/615,170, filed on Jan. 9, 2018.

(51) Int. Cl.
| | | |
|---|---|---|
| *A61K 31/472* | (2006.01) |
| *A61K 31/198* | (2006.01) |
| *A61K 31/225* | (2006.01) |
| *A61K 31/4418* | (2006.01) |
| *A61K 31/513* | (2006.01) |
| *A61K 31/5377* | (2006.01) |
| *A61P 11/00* | (2006.01) |
| *A61P 13/12* | (2006.01) |
| *C12N 15/113* | (2010.01) |

(52) U.S. Cl.
CPC .......... *A61K 31/472* (2013.01); *A61K 31/198* (2013.01); *A61K 31/225* (2013.01); *A61K 31/4418* (2013.01); *A61K 31/513* (2013.01); *A61K 31/5377* (2013.01); *A61P 11/00* (2018.01); *A61P 13/12* (2018.01); *C12N 15/1137* (2013.01)

(58) Field of Classification Search
CPC .. A61K 31/472; A61K 31/198; A61K 31/225; A61K 31/4418; A61K 31/513; A61K 31/5377; A61P 13/12; A61P 11/00; C12N 15/1137
USPC ........................................................ 546/139
See application file for complete search history.

(56) References Cited

U.S. PATENT DOCUMENTS

| | | |
|---|---|---|
| 6,093,730 A | 7/2000 | Weidmann et al. |
| 6,566,088 B1 | 5/2003 | McKnight et al. |
| 7,863,292 B2 | 1/2011 | Arend et al. |
| 8,278,325 B2 | 10/2012 | Arend et al. |
| 9,439,888 B2 | 9/2016 | Duncton et al. |
| 9,701,647 B2 | 7/2017 | Duncton et al. |
| 9,809,586 B2 | 11/2017 | Raines et al. |
| 10,517,839 B2 | 12/2019 | Silver et al. |
| 2007/0155784 A1 | 7/2007 | Arend et al. |
| 2016/0280701 A1 | 9/2016 | Raines et al. |
| 2019/0298709 A1 | 10/2019 | Silver et al. |

FOREIGN PATENT DOCUMENTS

| | | |
|---|---|---|
| WO | 2020/028745 A1 | 2/2020 |
| WO | 2020/055687 A1 | 3/2020 |

OTHER PUBLICATIONS

Kantari-Mimoun C. et al., "Boosting the Hypoxic Response in Myeloid Cells Accelerates Resolution of Fibrosis and Regeneration of the Liver in Mice", Oncotarget 8(9):15085-15100 (Feb. 28, 2017).
Moll S. et al., "Targeting the Epithelial Cells in Fibrosis: a New Concept for an Old Disease", Drug Discovery Today 18(11/12):582-591 (Jun. 2013).
Extended Supplementary European Search Report dated Sep. 15, 2021 received in European Application No. 19 73 8786.3.
Encylopaedia Britannica. "Double-stranded RNA—Biochemistry", <https://web.archive.org/web/20150908084728/https://www.britannica.com/science/doublestranded-RNA>; p. 1, para 1 (Sep. 8, 2015).
Gallant-Behm, C.L. et al., "The mast cell stabilizer ketotifen prevents development of excessive skin wound contraction and fibrosis in red Duroc pigs", Wound Rep Reg, vol. 16, pp. 226-233 (Mar. 2008).
Heber-Katz, E., "Oxygen, Metabolism, and Regeneration: Lessons from Mice", Trends Mol Med., vol. 23, issue 11, pp. 1024-1036 (Nov. 2017).
Hong, W.X. et al., "The Role of Hypoxia-Inducible Factor in Wound Healing", Advances in Wound Care, vol. 3, No. 5, pp. 390-399 (May 2014).
Kant, R. et al. "Prolyl 4 Hydroxylase: A Critical Target in the Pathophysiology of Diseases", Korean J Physiol Pharmacol., vol. 17, pp. 111-120 (Apr. 10, 2013).
Kiriakidis, S., et al. "Complement C1q is hydroxylated by collagen prolyl 4 hydroxylase and is sensitive to off-target inhibition by prolyl hydroxylase domain inhibitors that stabilize hypoxia-inducible factor", Kidney International, vol. 92, pp. 900-908 (Jun. 3, 2017).
International Search Report dated Apr. 23, 2019 together with the Written Opinion received in related International Application No. PCT/US19/12856.

*Primary Examiner* — Kristin A Vajda
(74) *Attorney, Agent, or Firm* — Scully, Scott, Murphy & Presser, P.C.

(57) ABSTRACT

The disclosure provides a method of treating fibrosis of an organ comprising administering a c-P4H inhibitor to a patient suffering from fibrosis in an organ, to counteract pathological fibrosis. c-P4H inhibitors can be administered via various routes, including in an aerosolized state using a nebulizer, intravenous, intraperitoneal or subcutaneous injection.

15 Claims, 23 Drawing Sheets
(21 of 23 Drawing Sheet(s) Filed in Color)

PREVENTION AND TREATMENT OF ORGAN FIBROSIS

CROSS REFERENCE TO RELATED APPLICATION

This application claims the benefit of priority from U.S. Provisional Application No. 62/615,170, filed on Jan. 9, 2018, and U.S. Provisional Application No. 62/699,424, filed on Jul. 17, 2018, the entire contents of which are incorporated herein by reference.

BACKGROUND

Fibrosis has been estimated to contribute to approximately 45% of deaths in the developed world. Fibrosis, which can be defined as the abnormal or excessive accumulation of extracellular matrix, particularly fibrillar collagens, is a key driver of progressive organ dysfunction in many inflammatory and metabolic diseases, including idiopathic pulmonary fibrosis, liver disease and kidney disease. These conditions remain poorly treated. There are few effective therapies and fewer that target fibrogenesis specifically. This highlights the need for a deeper comprehension of the pathogenesis of fibrogenesis and the translation of this knowledge to novel treatments.

Pulmonary fibrosis is scarring of lung tissue and idiopathic pulmonary fibrosis (IPF) which belongs to a large group of more than two hundred lung diseases, characterized by the involvement of lung interstitium, is defined as a specific form of chronic, progressive, irreversible fibrosing interstitial pneumonia of unknown cause, occurring in older adults. In the United States 100,000 people are living with idiopathic pulmonary and 42,000 more people aged 65 and older are diagnosed with IPF annually. The clinical course is described by progressive worsening of dyspnea and lung function and is associated with a poor prognosis. Treatment options are limited to halting progression of the disease and oxygen supplementation to improve symptoms and organ function. The clinical course of IPF includes acute exacerbations often with hospitalization.

Inflammation is central to the development of fibrosis in the lungs and inflammatory cells, including mast cells, are found in abundance in pulmonary fibrosis. Clinically, a correlation between severity of lung fibrosis and mast cell number is well documented. Previous work in a murine model of pulmonary fibrosis shows that mast cells play a significant contribution to pathologic collagen deposition. In the lungs, mast cells are found closely apposed to fibroblasts, the cells responsible for collagen synthesis and secretion. Mast cell mediators can be fibrogenic and stimulate collagen synthesis in human lung fibroblasts.

The assembly of collagen into its mature, triple helical form requires prolyl hydroxylation, which is the conversion of proline residues in procollagen to hydroxyproline. Collagen prolyl-4-hydroxylases (c-P4Hs) are the enzymes responsible for the prolyl hydroxylation. C-P4H enzymes are members of the superfamily of 2-oxoglutarate (2-OG)-dependent dioxygenases that have an Fe(II) atom at the active site and require oxygen and 2-OG as co-substrates. The catalytically active form of the c-P4H enzyme is a α-2β-2 tetramer which catalyzes the post-translational formation of hydroxyproline in collagens.

Another group of prolyl 4-hydroxylases are the prolyl hydroxylase domain (PHD) enzymes associated with hypoxia inducible factors (HIFs). HIF PHD enzymes are structurally related to c-P4H and also belong to the superfamily of 2-OG-dependent dioxygenases. There are multiple examples of HIF PHD antagonists that function as competitive inhibitors with structural similarity to 2-OG. These inhibitors can act as competitive antagonists of 2-OG, a cofactor that accepts one oxygen from molecular dioxygen to become succinate as the second oxygen forms trans-4-hydroxyproline.

SUMMARY OF THE DISCLOSURE

In one aspect, this disclosure provides a method of treating fibrosis of an organ in a patient in need of such treatment, comprising administering to the patient an effective amount of a collagen prolyl-4-hydroxylase (c-P4H) inhibitor. In some embodiments, the organ is selected from the group consisting of lung, kidney and liver.

In some embodiments, the c-P4H inhibitor is administered intermittently.

In some embodiments, the c-P4H inhibitor is administered every other day, every three days, every five days or once a week. In some embodiments, the c-P4H inhibitor is administered every hour, every two hours, every three hours, every six hours or every twelve hours.

In some embodiments, the c-P4H inhibitor is administered by intravenous (i.v.) injection, intraperitoneal (i.p.) injection, subcutaneous (s.c.) injection, or aerosolized delivery.

In some embodiments, the c-P4H inhibitor is a small molecule inhibitor. In some embodiments, the small molecule inhibitor of c-P4H is a prolyl hydroxylase domain (PHD) inhibitor. In some embodiments, the PHD inhibitor specifically inhibits the activity of c-P4H.

In some embodiments, wherein the PHD inhibitor is selected from the group consisting of Roxadustat (RXD) (FG-4592), Vadadustat (AKB-6548), Daprodustat (GSK-1278863), and Molidustat (BAY 85-3934).

In some embodiments, the PHD inhibitor is has the following chemical structure

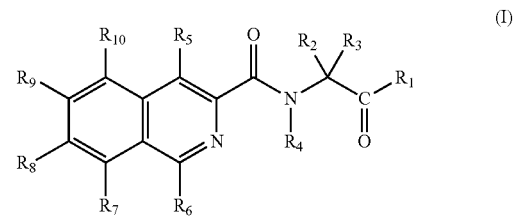

wherein:
R1 is selected from the group consisting of hydroxyl, alkoxy, substituted alkoxy, aryloxy, and substituted aryloxy;
R2 and R3 are independently selected from the group consisting of hydrogen, alkyl, substituted alkyl, cycloalkyl, substituted cycloalkyl, aryl, substituted aryl, heterocycloalkyl, substituted heterocycloalkyl, heteroaryl, and substituted heteroaryl; or
R2 and R3 together with the carbon atom to which they are attached form a cycloalkyl, substituted cycloalkyl, hererocycloalkyl, or substituted hererocycloalkyl;
R4 is selected from the group consisting of hydrogen, alkyl, and substituted alkyl;
R5 is selected from the group consisting of hydroxyl, alkoxy, and substituted alkoxy;

R6 is selected from the group consisting of hydrogen, alkyl, substituted alkyl, cycloalkyl, substituted cycloalkyl, cyano, halo, hydroxyl, alkoxy, substituted alkoxy, amino, substituted amino, arylozy, substituted arylozy, aminoacyl, substituted aminoacyl, cycloalkoxy, substituted cycloalkoxy, aryl, substituted aryl, aryloxy, substituted aryloxy, heterocycloalkyl, substituted heterocycloalkyl, heteroaryloxy, substituted heteroaryloxy, heteroaryl, and substituted heteroaryl; and R7, R8, R9 and R10 are independently selected from the group consisting of hydrogen, halo, alkyl, substituted alkyl, cycloalkyl, substituted cycloalkyl, aryl, substituted aryl, heteroaryl, substituted heteroaryl, alkoxy, substituted alkoxy, aryloxy, and substituted aryloxy.

In some embodiments, R6 is alkyl. In another embodiment, the alkyl at R6 is methyl.

In some embodiments, R5 is hydroxyl.

In some embodiments, R8 is aryloxy.

In some embodiments, wherein R6 is methyl and R5 is hydroxyl.

In a specific embodiment, the PHD inhibitor is FG-4592, wherein the FG-4592 has the chemical name N-[(4-hydroxy-1-methyl-7-phenoxyisoquinolin-3-yl)carbonyl]glycine)] and the following chemical structure:

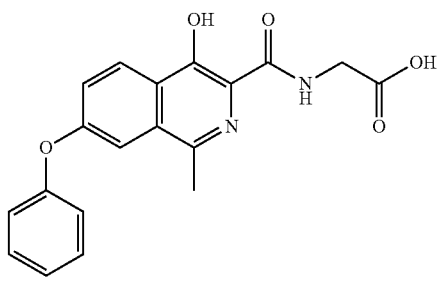

Roxadustat (FG-4592)

In some embodiments, the PHD inhibitor is administered in an amount between 0.2 mg/kg and 20 mg/kg. In some embodiments, the PHD inhibitor is administered at an amount between 50 mg/kg and 200 mg/kg.

In some embodiments, the PHD inhibitor is a 2-oxoglutarate analogue.

In a specific embodiment, the 2-oxoglutarate analogue is dimethyloxalylglycine (DMOG), wherein said DMOG has the chemical name N-(2-Methoxy-2-oxaoacetyl)glycine methyl ester) and the following chemical structure:

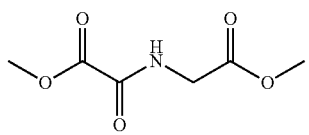

Dimethyloxalylglycine (DMOG)

In some embodiments, the DMOG is administered at an amount between 50 mg/kg and 200 mg/kg.

In some embodiments, the inhibition of the activity of the c-P4H enzyme is achieved by a method selected from the group consisting of introducing a nucleic acid inhibitor, the CRISPR/Cas system, the Cre/Lox system, the TALEN system, and homologous recombination.

In some embodiments, the nucleic acid inhibitor is selected from the group consisting of an antisense RNA, a small interfering RNA, an RNAi microRNA, an artificial microRNA, and a ribozyme.

Another aspect of this invention is directed towards an expression vector, comprising a nucleotide sequence that is transcribed into a nucleic acid inhibitor of expression of the c-P4H gene, operably linked to a regulatory region that is functional in a cell, wherein the nucleic acid is selected from the group consisting of an antisense RNA, a small interfering RNA, an RNAi microRNA, an artificial microRNA, and a ribozyme.

In some embodiments, the regulatory region comprises an inducible promoter, a tissue-specific promoter or an organ-specific promoter.

In some embodiments, the organ-specific promoter is selected from a group consisting of a lung-specific promoter, a kidney-specific promoter, and a liver-specific promoter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figures 1A, 1B, 1C:
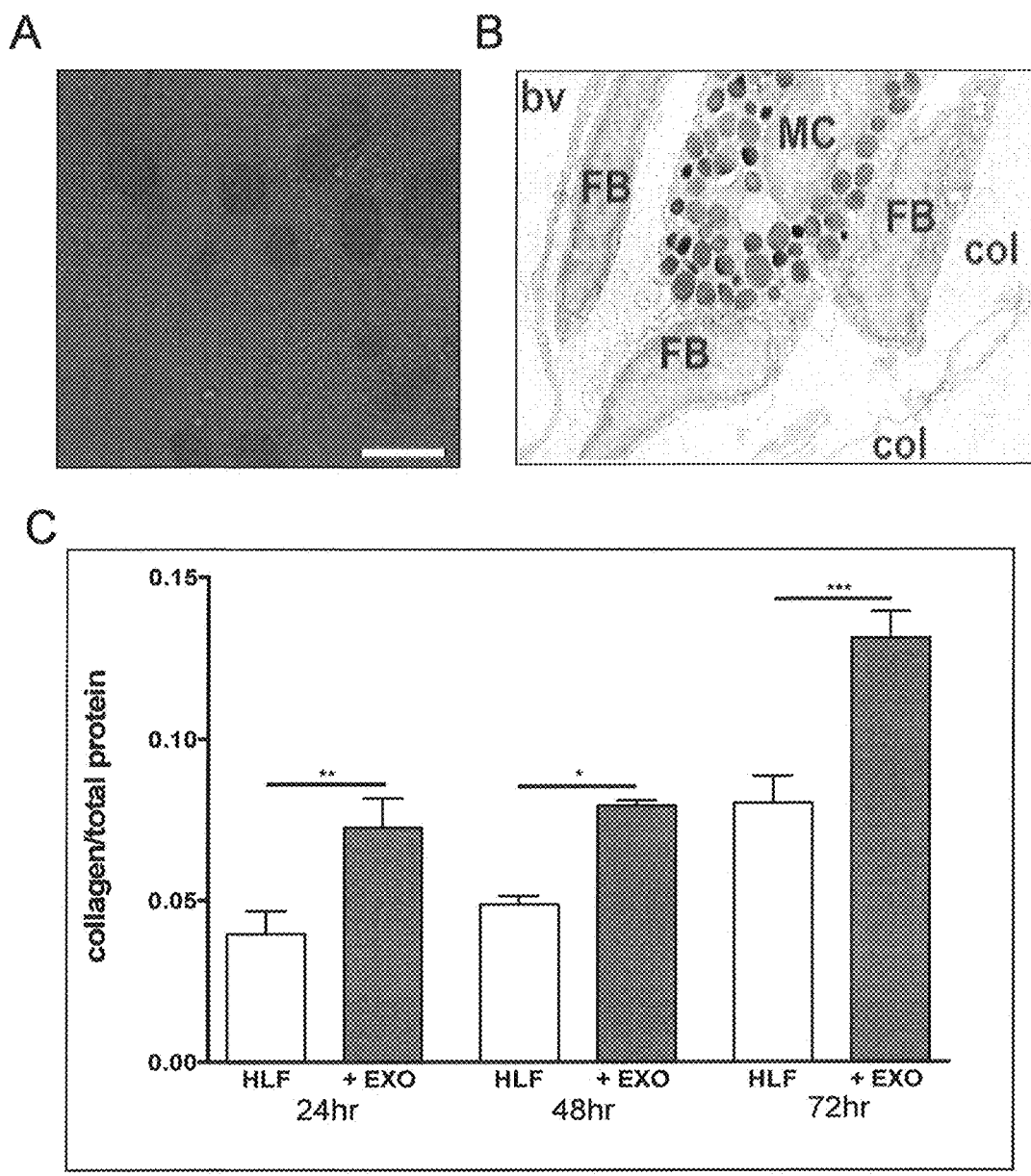
FIG. 1A-1C. A. Human lung fibroblasts take up mast cell exosomes labeled with fluorescent dye. Fibroblast nuclei are labeled with fluorescent DAPI. Viewed at 60× under transmitted light with fluorescence signal superimposed. B. Mast cells in close proximity to fibroblasts. Electron micrograph showing relationship between mast cells (MC), fibroblasts (FB), collagen (col) and blood vessels (bv). 7,500×. C. Exosomes (EXO) induce human lung fibroblast (HLF) collagen synthesis and secretion. HLF cells were co-cultured with EXO (40 ug/ml), supernatant was collected after 24, 48, and 72 hours for measurement of newly secreted collagen. Cell lysate was used to quantify total protein/well for normalization. Data are mean SEM of three separate experiments (n=3), each point run in triplicate. *P<0.05, P<0.01, *p<0.001.

An aspect of the present disclosure is predicated at least in part on modulating the collagen prolyl-4-hydroxylase (c-P4H) pathway for therapeutic purposes in the prevention, amelioration and/or attenuation of fibrosis in organs. The term "prevention" used herein means delay or eliminate the onset of fibrosis, or reduce the occurrences of fibrosis among a population of patients. The present disclosure is based on the finding that inhibiting the c-P4H enzyme is an effective antifibrotic method which prevents production of newly-synthesized collagen, without affecting existing collagen.

In some embodiments, the patient is suffering from fibrosis of the lung (lung fibrosis), kidney (kidney fibrosis) or liver (liver fibrosis).

In some embodiments, inhibiting c-P4H is achieved by a c-P4H inhibitor.

In one embodiment, a C-P4H inhibitor is not administered to the subject continuously; rather it is administered intermittently. In a specific embodiment, intermittent C-P4H inhibitor administration is performed once every other day, every three days, every four days, every five days, or once a week. In another specific embodiment, intermittent C-P4H inhibitor administration is performed once every hour, every two hours, every three hours, every six hours, every ten hours, or every twelve hours.

In some embodiments, an effective amount of a C-P4H inhibitor is about 0.2 mg/kg to 100 mg/kg. In other embodiments, the effective amount of a C-P4H inhibitor is about 0.2 mg/kg, 0.5 mg/kg, 1 mg/kg, 8 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 175 mg/kg or 200 mg/kg of C-P4H inhibitor.

In some embodiments, the C-P4H inhibitor is an agent that inhibits C-P4H hydroxylase activity. An agent that inhibits C-P4H hydroxylase activity is any agent that reduces or otherwise modulates the activity of a C-P4H hydroxylase enzyme.

In some embodiments, the c-P4H inhibitor is a small molecule compound. The term "small molecule compound" herein refers to small organic chemical compound, generally having a molecular weight of less than 2000 daltons, 1500 daltons, 1000 daltons, 800 daltons, or 600 daltons.

In some embodiments, the c-P4H inhibitor inhibits the prolyl hydroxylase domain (PHD) of c-P4H (PHD inhibitor).

In a specific embodiment, the PHD inhibitor specifically inhibits c-P4H. The term "specific c-P4H inhibitor" or "selective c-P4H inhibitor" refers to compounds or mixtures of compounds that selectively inhibit c-P4H over other members of the 2-oxogluterate (2-OG)-dependent dioxygenases superfamily.

In particular embodiments of the present invention, the agent that inhibits c-P4H hydroxylase activity is a structural mimetic of 2-oxoglutarate. Such compounds may inhibit the target 2-oxoglutarate dioxygenase enzyme family member competitively.

The general structure of HIF hydroxylase inhibitors for use in this invention is

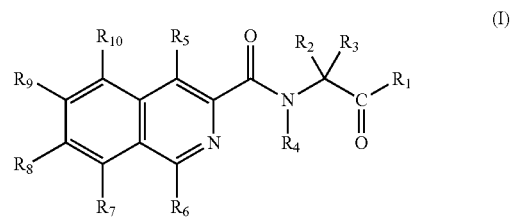

(I)

wherein:
R1 is selected from the group consisting of hydroxyl, alkoxy, substituted alkoxy, aryloxy, and substituted aryloxy;
R2 and R3 are independently selected from the group consisting of hydrogen, alkyl, substituted alkyl, cycloalkyl, substituted cycloalkyl, aryl, substituted aryl, heterocycloalkyl, substituted heterocycloalkyl, heteroaryl, and substituted heteroaryl; or
R2 and R3 together with the carbon atom to which they are attached form a cycloalkyl, substituted cycloalkyl, hererocycloalkyl, or substituted hererocycloalkyl;
R4 is selected from the group consisting of hydrogen, alkyl, and substituted alkyl;
R5 is selected from the group consisting of hydroxyl, alkoxy, and substituted alkoxy;
R6 is selected from the group consisting of hydrogen, alkyl, substituted alkyl, cycloalkyl, substituted cycloalkyl, cyano, halo, hydroxyl, alkoxy, substituted alkoxy, amino, substituted amino, arylozy, substituted arylozy, aminoacyl, substituted aminoacyl, cycloalkoxy, substituted cycloalkoxy, aryl, substituted aryl, aryloxy, substituted aryloxy, heterocycloalkyl, substituted heterocycloalkyl, heteroaryloxy, substituted heteroaryloxy, heteroaryl, and substituted heteroaryl; and
R7, R8, R9 and R10 are independently selected from the group consisting of hydrogen, halo, alkyl, substituted alkyl, cycloalkyl, substituted cycloalkyl, aryl, substituted aryl, heteroaryl, substituted heteroaryl, alkoxy, substituted alkoxy, aryloxy, and substituted aryloxy.

In some embodiments, R6 is alkyl. In another embodiment, the alkyl at R6 is methyl.

In some embodiments, R5 is hydroxyl.

In some embodiments, R8 is aryloxy.

In some embodiments, wherein R6 is methyl and R5 is hydroxyl.

As used herein, the term "alkyl" refers to a straight or branched, saturated hydrocarbon group having 1 to 10 carbon atoms, more particularly from 1 to 5 carbon atoms, and even more particularly 1 to 3 carbon atoms. Representative alkyl groups include methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)2-alkyl, —OS(O)2-substituted alkyl, —OS(O)2-aryl, —OS(O)2-substituted aryl, —OS(O)2-heteroaryl, —OS(O)2-substituted heteroaryl, —OS(O)2-heterocyclic, —OS(O)2-substituted heterocyclic, and —OSO2-NR11R11, —NR11S(O)2-NR11-alkyl, —NR11S(O)2-NR11-substituted alkyl, —NR11S(O)2-NR11-aryl, —NR11S(O)2-NR11-substituted aryl, —NR11S(O)2-NR11-heteroaryl, —NR11S(O)2-NR11-substituted heteroaryl, —NR11S(O)2-NR11-heterocyclic, and —NR11S(O)2-NR11-substituted heterocyclic, wherein each R11 is independently selected from hydrogen or alkyl. Representative substituted alkyl groups include trifluoromethyl, benzyl, pyrazol-1-ylmethyl and the like.

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide" refers to the group —C(O)NR12R12, wherein each R12 is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or wherein each R12 is joined to form together with the nitrogen atom a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Representative alkenyl groups include vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. Representative alkynyl groups include ethyn-1-yl, propyn-1-yl, propyn-2-yl, and the like.

The term "amino" refers to the group —NH2.

The term "substituted amino" refers to the group —NR13R13, wherein each R13 is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R13 groups are not hydrogen; or the R13 groups can be joined together with the nitrogen atom to form a heterocyclic or substituted heterocyclic ring. Representative substituted amino groups include phenylamino, methylphenylamino, and the like. Representative substituted amino groups include (ethanic acid-2-yl)amino, and the like.

The term "acylamino" refers to the groups —NR14C(O)alkyl, —NR14C(O)substituted alkyl, —NR14C(O)cycloalkyl, —NR14C(O)substituted cycloalkyl, —NR14C(O)alkenyl, —NR14C(O)substituted alkenyl, —NR14C(O)alkynyl, —NR14C(O)substituted alkynyl, —NR14C(O)aryl, —NR14C(O)substituted aryl, —NR14C(O)heteroaryl, —NR14C(O)substituted heteroaryl, —NR14C(O)heterocyclic, and —NR14C(O)substituted heterocyclic, wherein R14 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR15C(O)O-alkyl, —NR15C(O)O-substituted alkyl, —NR15C(O)O-alkenyl, —NR15C(O)O-substituted alkenyl, —NR15C(O)O-alkynyl, —NR15C(O)O-substituted alkynyl, —NR15C(O)O— cycloalkyl, —NR15C(O)O-substituted cycloalkyl, —NR15C(O)O-aryl, —NR15C(O)O— substituted aryl, —NR15C(O)O-heteroaryl, —NR15C(O)O-substituted heteroaryl, —NR15C(O)O-heterocyclic, and —NR15C(O)O-substituted heterocyclic, wherein R15 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR16C(S)O-alkyl, —NR16C(S)O-substituted alkyl, —NR16C(S)O-alkenyl, —NR16C(S)O-substituted alkenyl, —NR16C(S)O-alkynyl, —NR16C(S)O-substituted alkynyl, —NR16C(S)O-cycloalkyl, —NR16C(S)O-substituted cycloalkyl, —NR16C(S)O-aryl, —NR16C(S)O-substituted aryl, —NR16C(S)O-heteroaryl, —NR16C(S)O-substituted heteroaryl, —NR16C(S)O-heterocyclic, and —NR16C(S)O-substituted heterocyclic, wherein R16 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —OC(O)NR17R17, wherein each R17 is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or wherein each R17 is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR18C(O)—NR18R18, wherein each R18 is independently selected from the group consisting of hydrogen and alkyl.

The term "aminothiocarbonylamino" refers to the group —NR19C(S)—NR19R19, wherein each R19 is independently selected from the group consisting of hydrogen and alkyl.

The term "aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)2-alkyl, —OS(O)2-substituted alkyl, —OS(O)2-aryl, —OS(O)2-substituted aryl, —OS(O)2-heteroaryl, —OS(O)2-substituted heteroaryl, —OS(O)2-heterocyclic, —OS(O)2-substituted heterocyclic, and —OSO2-NR20R20, —NR20S(O)2-NR20-alkyl, —NR20S(O)2-NR20-substituted alkyl, —NR20S(O)2-NR20-aryl, —NR20S(O)2-NR20-substituted aryl, —NR20S(O)2-NR20-heteroaryl, —NR20S(O)2-NR20-substituted heteroaryl, —NR20S(O)2-NR20-heterocyclic, —NR20S(O)2-NR20-substituted heterocyclic, wherein each R20 is independently selected from hydrogen or alkyl, and wherein each of the terms is as defined herein. Representative substituted aryl groups include 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, and the like.

The term "aryloxy" refers to the group aryl-O— that includes, by way of example, phenoxy, naphthoxy and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O— substituted alkyl, —C(O)O-alkenyl, —C(O)O-substituted alkenyl, —C(O)O-alkynyl, —C(O)O-substituted alkynyl, —C(O)β-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Representative heteroaryl groups include pyridinyl, pyrimidinyl, pyrrolyl, pyrazolyl, indolyl, thiophenyl, thienyl, furyl, and the like.

The term "substituted heteroaryl" refers to heteroaryl groups that are substituted with from 1 to 3 substituents selected from the same group of substituents defined for substituted aryl. Representative substituted heteroaryl groups include 5-fluoro-pyridin-3-yl, 1-benzyl-1H-[1,2,3]triazol-4-yl, 5-bromo-furan-2-yl, trifluoromethyl-2H-pyrazol-3-yl, and the like.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring, wherein in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO2.

The term "oxo" refers to the atom (=O) or to the atom (—O—).

The term "sulfonyl" refers to the group —S(O)2H.

The term "substituted sulfonyl" refers to the group —SO2-alkyl, —SO2-substituted alkyl, —SO2-alkenyl, —SO2-substituted alkenyl, —SO2-alkynyl. —SO2-substituted alkynyl, —SO2-cycloalkyl, —SO2-substituted cycloalkyl, —SO2-cycloalkenyl, —SO2-substituted cycloalkenyl, —SO2-aryl. —SO2-substituted aryl, —SO2-heteroaryl. —SO2-substituted heteroaryl, —SO2-heterocyclic, —SO2-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Representative sulfonyl groups include methyl-SO2-, phenyl-SO2-, 4-methylphenyl-SO2-, and the like.

The term "heterocyclyloxy" refers to the group —O-heterocyclic, and "substituted heterocyclyloxy" refers to the group —O-substituted heterocyclic.

The term "thio" refers to the group —SH.

The term "alkylsulfanyl," "alkylthio," or "thioether" refers to the groups —S-alkyl, wherein alkyl is as defined above.

The term "substituted alkylthio," "substituted alkylsulfanyl," or "substituted alkylthio" refers to the group —S-substituted alkyl, wherein substituted alkyl is as defined above.

The term "cycloalkylthio" or "cycloalkylsulfanyl" refers to the groups —S— cycloalkyl wherein cycloalkyl is as defined above.

The term "substituted cycloalkylthio" refers to the group —S-substituted cycloalkyl wherein substituted cycloalkyl is as defined above.

The term "arylthio" or "arylsulfanyl" refers to the group —S-aryl, and "substituted arylthio" refers to the group —S-substituted aryl, wherein aryl and substituted aryl are as defined above.

The term "heteroarylthio" or "heteroarylsulfanyl" refers to the group —S— heteroaryl, and "substituted heteroarylthio" refers to the group —S-substituted heteroaryl, wherein heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic wherein heterocyclic, and substituted heterocyclic are as defined above.

The term "ester" refers to the group —C(O)OR21, wherein R21 is alkyl, substituted alkyl, aryl, or substituted aryl.

In one embodiment, in Formula (1), R1 and R5 are hydroxyl; R2, R3, R4, R7, R9, and R10 are hydrogen; R6 is methyl; and R8 is phenox, and the compound has a structure shown below in formula (11). This molecule is also known as FG-4592 (aka. Roxadustat), which is an isoquinolone having the chemical name, N-[(4-hydroxy-1-methyl-7-phenoxyisoquinolin-3-yl)carbonyl]glycine)].

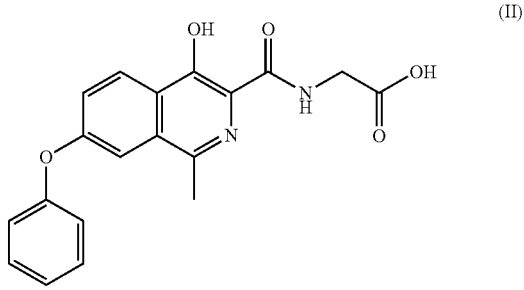 [SMILES: Cc1nc(C(=O)NCC(=O)O)c(O)c2ccc(Oc3ccccc3)cc12]
(II)

FG-4592 (Roxadustat) is in phase 3 clinical trials for the treatment of anemia in chronic kidney disease with no untoward effects reported.

In a specific embodiment, FG-4592 (Roxadustat) is administered at an amount between 0.2 mg/kg and 20 mg/kg. In another embodiment the dosage of FG-4592 (Roxadustat) is 0.2 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 18 mg/kg, or 20 mg/kg.

In some embodiments, a FG-4592 (Roxadustat) analogue is used. FG-4592 analogues are described in U.S. Pat. Nos. 9,701,647; 9,439,888; 7,863,292; and U.S. patent application Ser. Nos. 13/186,351 and 11/549,571, which are all incorporated by reference in their entirety.

In another specific embodiment, the C-P4H inhibitor is dimethyloxalylglycine (DMOG, amino dicarboxylic acid with flanking methyl groups; chemical name N-(2-Methoxy-2-oxaoacetyl)glycine methyl ester). DMOG has the flowing chemical structure:

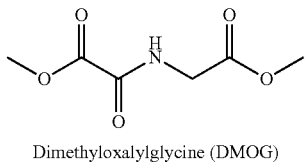
Dimethyloxalylglycine (DMOG)

In a specific embodiment, DMOG is administered at an amount between 50 mg/kg and 200 mg/kg. In another embodiment the dosage of DMOG is 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg. 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, or 200 mg/kg.

In an embodiment, a C-P4H inhibitor can be combined with a pharmaceutically acceptable carrier prior to administration. For the purposes of this disclosure, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

A C-P4H inhibitor can be admixed with a pharmaceutically acceptable carrier to make a pharmaceutical preparation in any conventional form including, inter alia, a solid form such as tablets, capsules (e.g. hard or soft gelatin capsules), pills, cachets, powders, granules, and the like; a liquid form such as solutions, suspensions; or in micronized powders, sprays, aerosols and the like.

In some embodiments, the composition of the present disclosure can be administered by different routes of administration such as oral, oronasal, or parenteral route.

"Oral" or "peroral" administration refers to the introduction of a substance into a subject's body through or by way of the mouth and involves swallowing or transport through the oral mucosa (e.g., sublingual or buccal absorption) or both.

"Oronasal" administration refers to the introduction of a substance into a subject's body through or by way of the nose and the mouth, as would occur, for example, by placing one or more droplets in the nose. Oronasal administration involves transport processes associated with oral and intranasal administration.

"Parenteral administration" refers to the introduction of a substance into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration.

In some embodiments, compositions comprising a C-P4H inhibitor can be administered by aerosol. For example, this can be accomplished by preparing an aqueous aerosol, liposomal preparation or solid particles containing a composition comprising a C-P4H inhibitor preparation. A non-aqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound.

In another aspect of the present disclosure, a C-P4H inhibitor is used in a method of preventing CLD in preterm neonates. In a specific embodiment a C-P4H inhibitor is administered to a preterm at a dose between 0.2 mg/kg and 200 mg/kg, depending on the C-P4H inhibitor used and the route of administration chosen. In other embodiments, the C-P4H inhibitor is administered at a dose about 0.2 mg/kg, 0.5 mg/kg, 1 mg/kg, 2 mg/kg, 3 mg/kg, 5 mg/kg, 8 mg/kg, 10 mg/kg, 15 mg/kg. 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg. 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, or 200 mg/kg of C-P4H inhibitor.

In yet another embodiment, a C-P4H inhibitor is administered to a patient in need thereof every day. In another embodiment a C-P4H inhibitor is administered intermittently every two days or every three days. In yet another embodiment, a C-P4H inhibitor is administered during oxygen supplementation sessions, and C-P4H inhibitor administration is stopped once the neonate is no longer on supplemental oxygen. In a specific embodiment C-P4H inhibitor are administered once a week. Administration of C-P4H inhibitor can be continued until the neonate can breathe on its own in room air.

In some embodiments, the PHD inhibitor is selected from the group consisting of Roxadustat (RXD) (FG-4592), Vadadustat (AKB-6548), Daprodustat (GSK-1278863), and Molidustat (BAY 85-3934).

In some embodiments, c-P4H inhibitor is an inhibitor selected from the group consisting of introducing a nucleic acid inhibitor, the CRISPR/Cas system, the Cre/Lox system, the TALEN system, and homologous recombination.

In some embodiments, the nucleic acid inhibitor of c-P4H inhibits expression of the c0P4H gene. In a specific embodiment, the nucleic acid inhibitor of c-P4H is selected from the group consisting of an antisense RNA, a small interfering RNA, an RNAi microRNA, an artificial microRNA, and a ribozyme.

Another aspect of the disclosure is directed to an expression vector, comprising a nucleotide sequence that is transcribed into a nucleic acid inhibitor of expression of the c-P4H gene, operably linked to a regulatory region that is functional in a cell, wherein the nucleic acid is selected from the group consisting of an antisense RNA, a small interfering RNA, an RNAi microRNA, an artificial microRNA, and a ribozyme.

In some embodiments, the regulatory region comprises an inducible promoter, a tissue-specific promoter or an organ-specific promoter. In a specific embodiment, the organ-specific promoter is selected from a group consisting of a lung-specific promoter, a kidney-specific promoter, and a liver-specific promoter.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Mast Cell Exosomes Taken Up by Lung Fibroblasts Stimulate Collagen Synthesis and Secretion: A Novel Means of Fibroblast Activation Fibroblasts and mast cells are found in close proximity in tissue (FIG. 1B). Mast cells shed particles, exosomes, that range in size from 20-100 nm and contain RNA and protein. The analysis of mast cell exosome protein content by mass spectrophotometry reveals that mast cell exosomes contain proteins like annexin 2 and the $\beta$-subunit of c-P4H, involved with fibrogenesis. Fibroblasts incubated with mast cell exosomes internalize the exosomes as shown in FIG. 1A. The representative micrograph of superimposed transmitted and fluorescent light images (FIG. 1A) shows that mast cell exosomes (green dots) are internalized by the fibroblasts (transmitted light). Following internalization, the exosomes activate the fibroblasts to secrete newly formed collagen (FIG. 1C). Activation occurred as early as 24 h ($P<0.01$) and continued to stimulate human lung fibroblast collagen production and secretion at 48 h ($P<0.05$) and up to 72 h ($P<0.001$) (FIG. 1C).

Figure 2A:
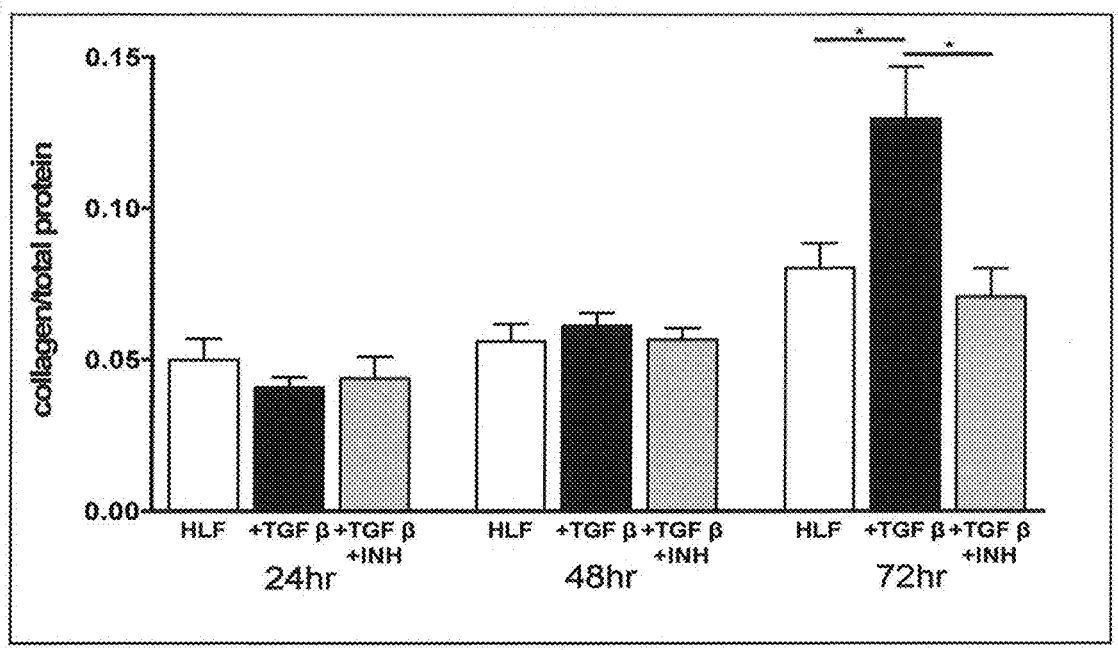
FIG. 2A-2C. A. Effect of TGF-β1 (10 ng/ml) on human lung fibroblast (HLF) collagen secretion, ±combined treatment using TGF βR1 inhibitor SB 543554 (1 uM) after 24, 48 and 72 hours. Cell lysate was used to quantify total protein/well for normalization. Data are mean±SEM of three separate experiments, (n=3), each point run in triplicate. *P<0.05. B. Effects of combined treatment with TGF-β1 (10 ng/ml) or exosomes (EXO) (40 ug/ml), ±TGF-βR1 inhibition. Cell lysate was used to quantify total protein/well for normalization. Data are mean±SEM of three separate experiments, n=3, each point run in triplicate. *P<0.05, **P<0.01. C. Western blot of human lung fibroblasts (HLF) homogenates probed for phosphorylated and non-phosphorylated Smad2 and Smad3, canonical TGF-b signaling mediators. Cell lysates were prepared after 24 hours of treatment with either TGF-β1 (10 ng/ml), or exosomes (EXO) (40 ug/ml). GAPDH was used as a housekeeping gene.

Example 2: Activation of Lung Fibroblasts by Mast Cell Exosomes and TGF-$\beta$ is Additive Via Different Pathways Exosomal activation of human lung fibroblasts was compared to the classical TGF-$\beta$1 stimulation of human lung fibroblasts. TGF-$\beta$1 stimulation of human lung fibroblasts collagen secretion follows a different time course from the exosome-induced collagen secretion, with a 48 h time lag. Exogenous addition of TGF-$\beta$1 caused significant collagen secretion by human lung fibroblasts at the 72 h time point ($P<0.05$) (FIG. 2A versus FIG. 1B).

Figure 2B:
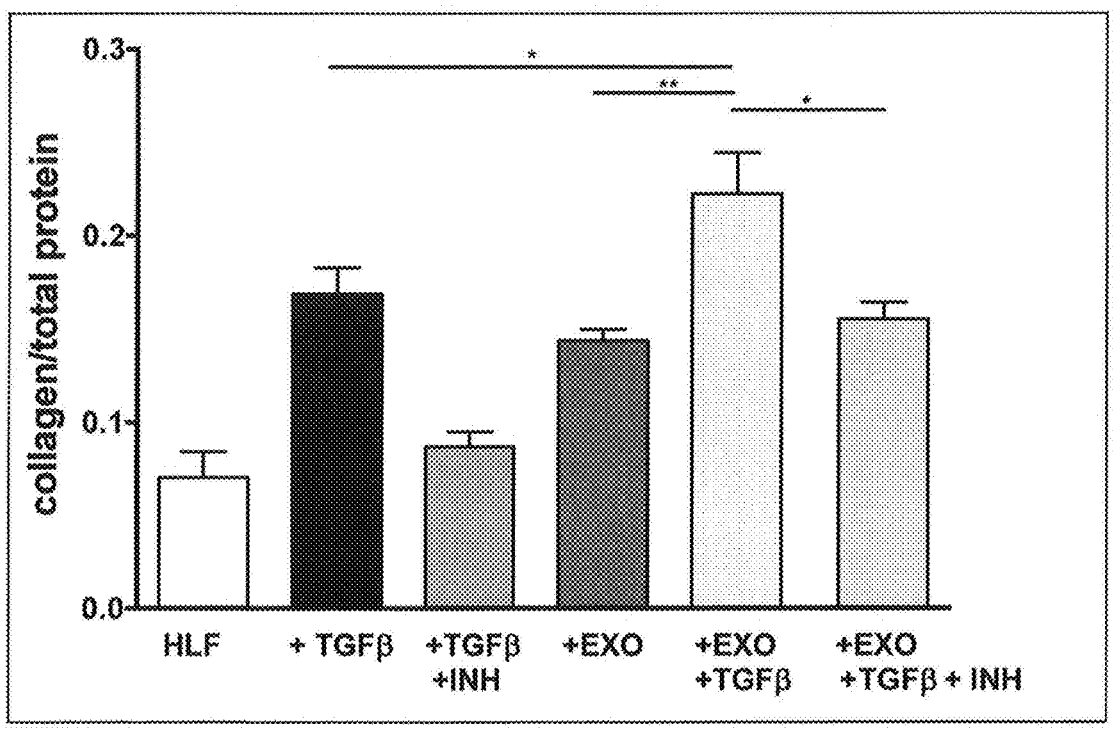

Incubating the human lung fibroblasts with exosomes and TGF-$\beta$1 is additive with collagen secretion being significantly greater in human lung fibroblasts exposed to both exosomes and TGF-$\beta$1 compared to TGF-$\beta$1 alone ($P<0.05$) or exosomes alone ($P<0.01$), respectively (FIG. 2B).

Figure 2C:
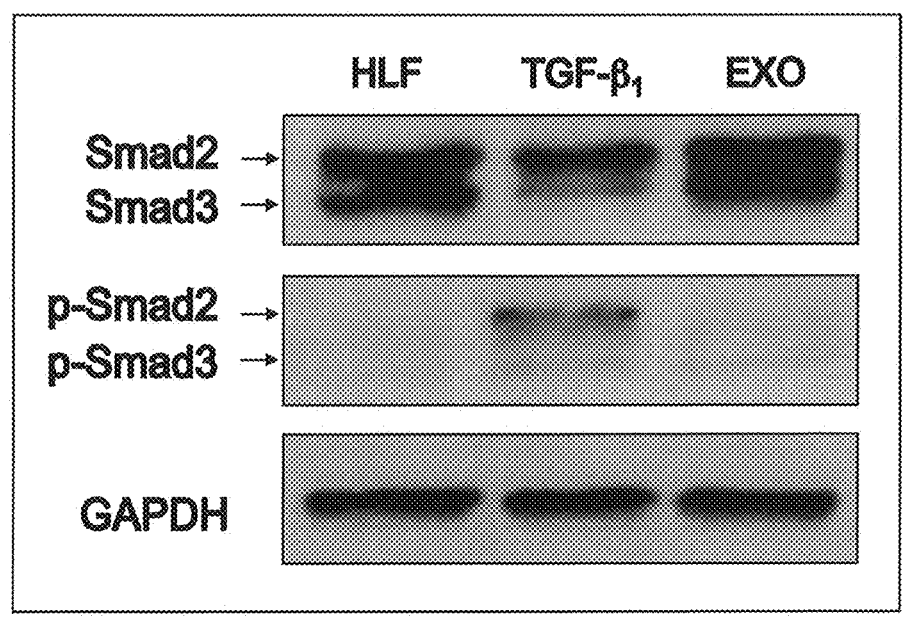

To determine if TGF-$\beta$1 and exosomes utilize the same signaling pathway for stimulating human lung fibroblasts collagen secretion, western blotting was performed on human lung fibroblast homogenates. Exposing human lung fibroblasts to TGF-$\beta$1 resulted in phosphorylation of SMAD, as expected. This was not observed in the exosome-exposed human lung fibroblasts (FIG. 2C). These results show that exosomes can stimulate secretion of newly synthesized collagen in human lung fibroblasts as does TGF-$\beta$1 though with different temporal courses. This suggests the involvement of different intracellular mechanisms for activating collagen synthesis in human lung fibroblasts, confirmed by the SMAD results.

The results in FIG. 1 and FIG. 2 point to a novel fibrogenic pathway by which mast cells and fibroblasts communicate in the lung representing an additional therapeutic target for blocking pulmonary fibrosis.

Example 3: HIF PHD Enzyme Inhibitors Block Human Lung Fibroblast Activity Collagen Synthesis and Secretion, Proliferation and Migration Because both the HIF PHD and c-P4H enzymes are structurally similar and belong to the 2-oxoglutarate (2-OG)-dependent dioxygenases superfamily, it was reasoned that HIF PHD antagonists that function as analogs of 2-OG, a cofactor that accepts one oxygen from molecular dioxygen to become succinate as the second oxygen forms trans-4-hydroxyproline, can also block c-P4H enzymatic activity. C-P4H is necessary for the assembly of newly formed collagen.

Figures 3A, 3B, 3C, 3D:
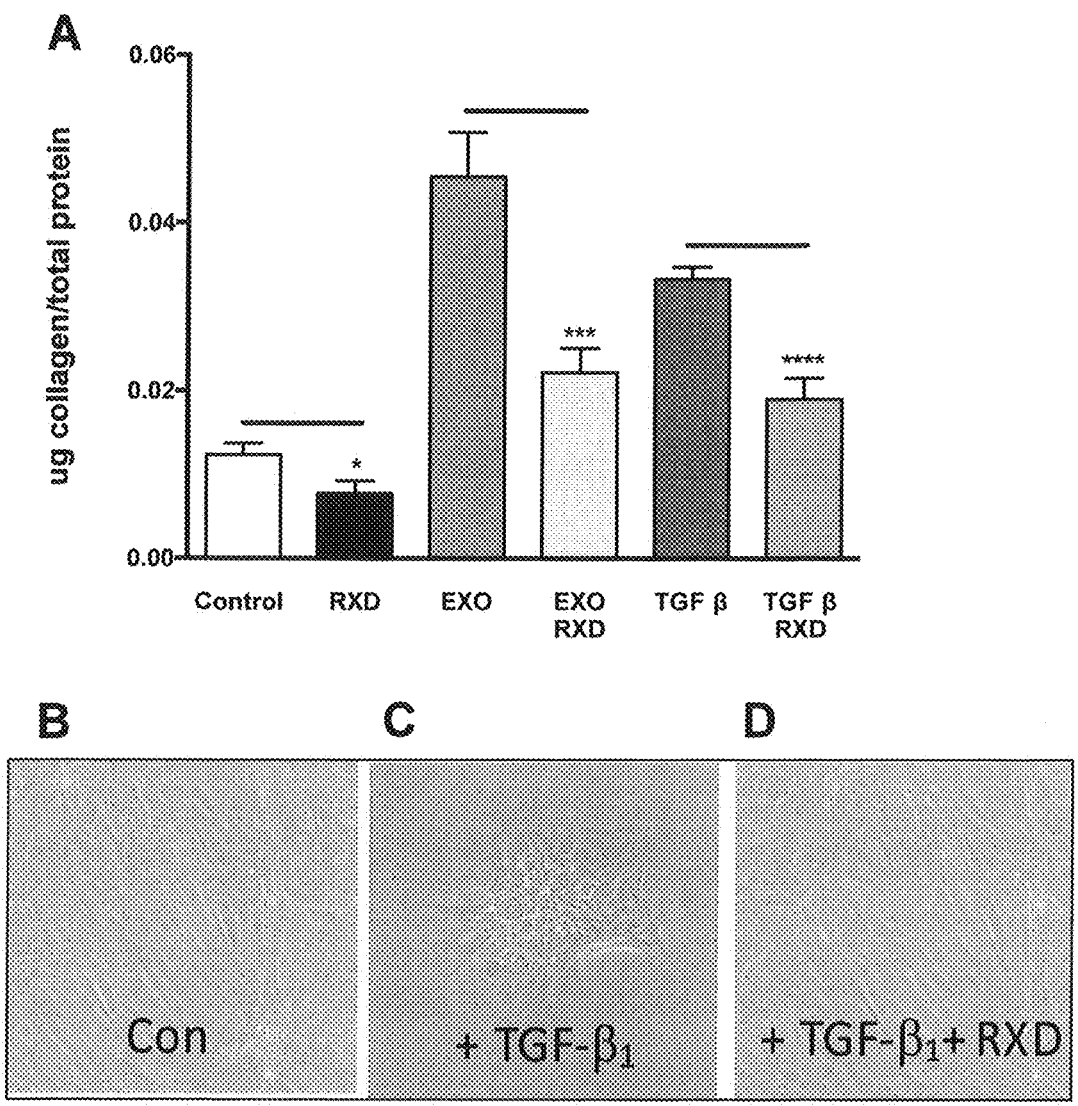
FIG. 3A-3E A. Roxadustat (RXD), the HIF PHD inhibitor, decreases constitutive, TGF-β- and exosome (EXO)-induced human lung fibroblast collagen secretion in human lung fibroblasts. Human lung fibroblasts were exposed to TGF-β (10 ng/ml) or co-cultured with EXO (40 μg/ml), and supernatants were collected for measurement of newly secreted collagen. RXD was used at 10 μg/ml. Cell lysates were used to quantify total protein/well for normalization. Data are means SEM of three separate experiments (n=3), each point run in triplicate. *P<0.05, *P<0.001, *P<0.0001. B.-E. RXD prevents fibroblast migration/accumulation/foci observed with TGF-β. Low magnification representative images of human lung fibroblasts in transwell plates untreated (Con) (B), +TGF-β (10 ng/ml) (C), or +TGF-β+RXD (10 mg/ml) (D) & (E). RXD decreases smooth muscle actin (SMA) abundance in human lung fibroblasts.

RXD and Collagen Secretion: In vitro experiments with human lung fibroblasts show that RXD inhibits collagen secretion in untreated fibroblasts, fibroblasts co-cultured with mast cell exosomes, and fibroblasts exposed to exogenous TGF-$\beta$1, the classic inductor of collagen synthesis. (FIG. 3A). All values presented are normalized for total protein.

RX and Fibroblast Proliferation: The data in FIG. 3B-3D show that RXD also blocks TGF-$\beta$ fibroblast proliferation as determined by total protein content of fibroblast cell lysates: control—0.800 μg/ml/well (FIG. 3B) versus +TGF-$\beta$ 1.138 μg/ml/well (FIG. 3C) versus +RXD+TGF-$\beta$ 0.828 μg/ml/well (FIG. 3D).

Figure 3E:
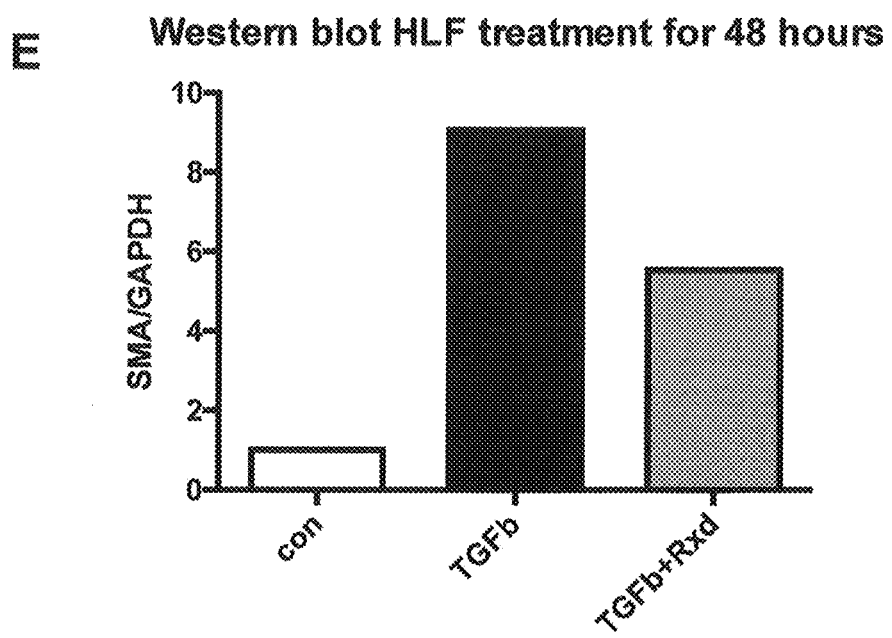

RXD and Fibroblast Migration/Accumulation/FOCI Formation and Fibroblast Activation via Smooth Muscle Actin (SMA): Qualitative data also show that RXD treatment prevents fibroblast migration, accumulation, and foci formation (Compare FIG. 3B-FIG. 3D). Western blotting shows that SMA abundance is also decreased with RXD in lung fibroblasts (FIG. 3E).

Figures 18A, 18B, 18C, 18D, 18E:
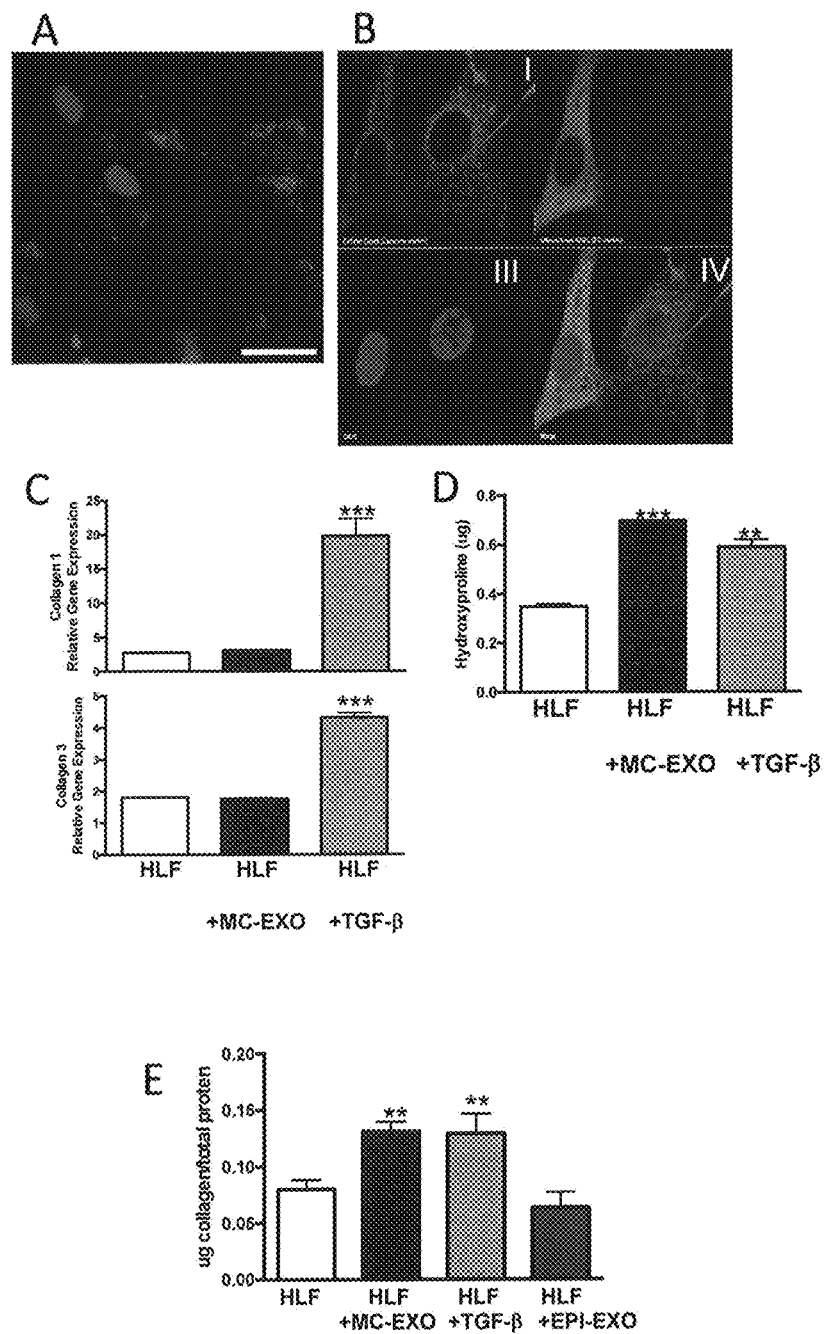
FIG. 18A-18E. Uptake of MC-EXOs by HLFs stimulates collagen synthesis by a Smad-independent pathway. A. HLF uptake of MC-EXO, labeled with PKH-67 (green). Nuclei are labeled with DAPI (blue). Viewed with an inverted epifluorescence microscope. Scale bar=15 uM. B. Confocal images of: I. Labeled MC-EXOs (CellVue Claret Far Red), II. HLF transiently transfected with mNeonGreen-KDEL, a fluorescent marker of the ER, III. DAPI labeled HLF showing nuclei, IV. Superimposed images (I.II.III) showing uptake of MC-EXO in the HLF ER. C. Lysates from HLF-treated with EXO (40 µg), and TGF-β (ng/ml) were harvested 72 h after treatment and RT qPCR performed for collagen I and collagen 3 relative gene expression normalized to GAPDH. D. Hydroxyproline content of lysates from HLF incubated with MC-EXO (40 ug) or TGF-β (10 ng/ml). E. Secreted collagen was measured in the supernatants from HLF, HLF+MC-EXO (40 ul), TGF-β (10 ng/ml), and HLF+EPI-EXO. Collagen was measured by Sircol assay. All assays performed in triplicate. P<0.01; *P<0.001 versus HLF.
Figures 19A, 19B, 19C, 19D, 19E:
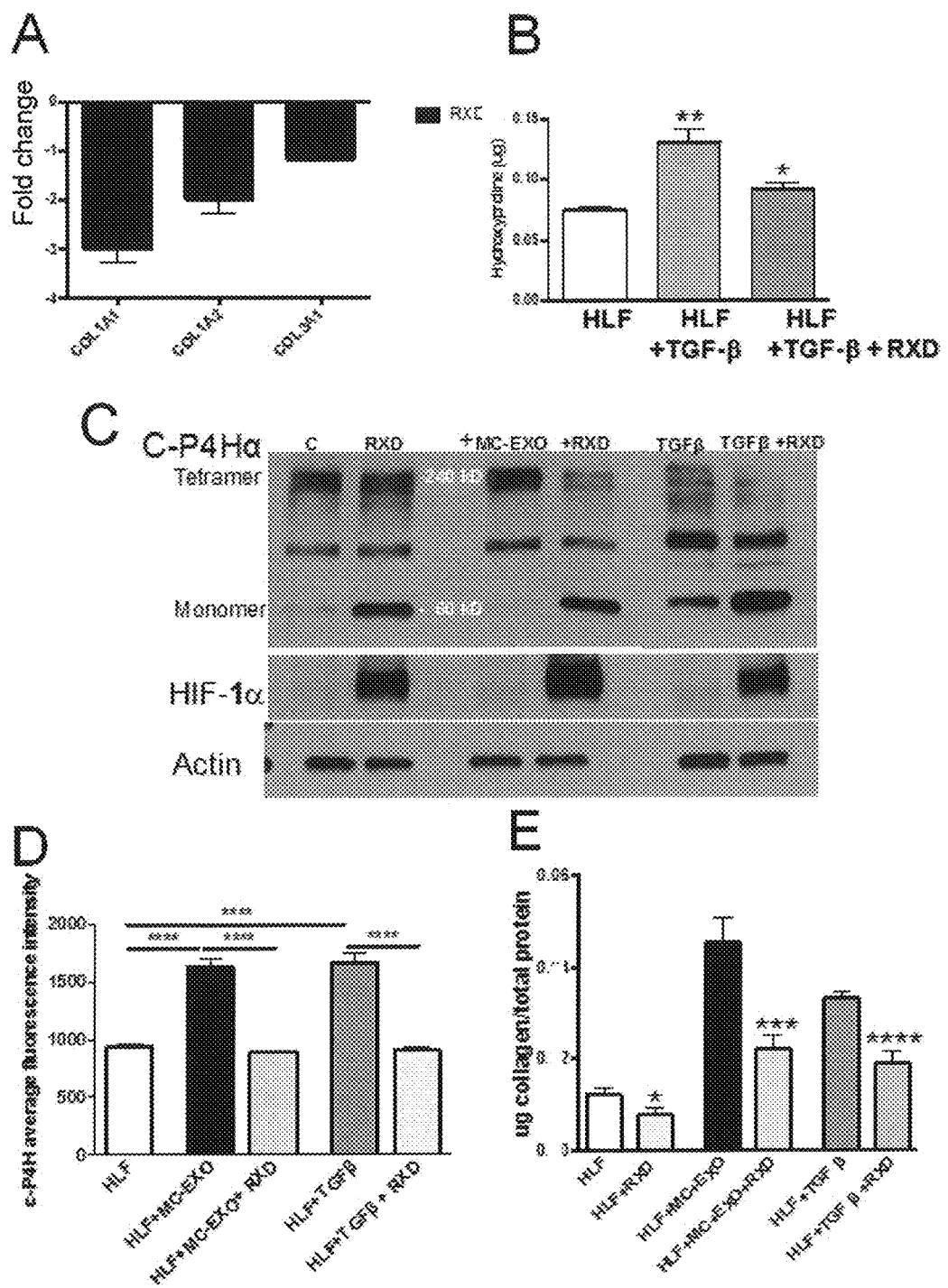
FIG. 19A-19E. In HLF RXD inhibits proline hydroxylation, hydroxyproline, C-P4H abundance and secreted collagen. A. LC-MC analysis of HLF extracted proteins shows that RXD prevented proline hydroxylation in collagens 1 and 3. B. RXD inhibited the TGF-β-induced increase in hydroxyproline in HLFs. C. RXD decreased C-P4H abundance in HLF lysates+MC-EXO and +TGFβ in Western blots. Actin was run as the loading control. D. RXD inhibited the increase in C-P4H fluorescence intensity measured in HLF+MC-EXO and HLF+TGF-β. E. Secreted collagen (Sircol) was blocked with RXD in HLF lysates from HLF untreated and treated with +MC-EXO and +TGF-β. *P<0.05; P<0.01; *P<0.001, ****P<0.0001 versus HLF. All assays were performed in triplicate.

Example 4: Uptake of MC-EXOs by HLFs Stimulates Collagen Synthesis by a Smad-Independent Pathway Using freshly isolated HLFs from normal waste tissue specimen and MC-EXOs harvested from human mastocytoma cell (HMC-1) supernatants, in vitro experiments demonstrate that MC-EXOs, labeled with the dye, PHK-67 (fluorescein-green) are taken up by HLFs as viewed with an inverted epifluorescence microscope (FIG. 18A). This uptake was confirmed with confocal imaging (FIG. 18B) and shows labeled MC-EXOs (CellVue Claret Far Red) localized to the endoplasmic reticulum (ER) in HLFs transiently transfected using Lipofectamine2000 with mNeon-Green-KDEL, a fluorescent marker of the ER (FIG. 18B-II). After 24 h of transient transfection the cells were exposed for 60 minutes to the labeled MC-EXO and then imaged on a Zeiss Observed SD spinning disk confocal microscope. As in the representative image, MC-EXO uptake (red) was robust in the HLFs (FIGS. 18B-I, IV) and in the successfully transfected HLF, appear in the ER. The nuclei of the HLFs are stained with DAPI (FIG. 18B-III).

MC-EXO uptake by HLF does not lead to phosphorylation of Smad (FIG. 2C) or stimulation of collagen I or collagen 3 gene expression (FIG. 18C) unlike that observed with TGF-β. However, MC-EXOs as well as TGF-β leads to increased HLF production of hydroxyproline content (FIG. 18D) and collagen secretion (FIG. 18E) (72 h time point). In parallel experiments HLFs incubated with lung epithelial cell (EPI) EXOs did not increase collagen secretion (FIG. 1E red bar—72 h time point) suggesting that uptake of EXO and stimulation of collagen synthesis in HLFs is not a generalized phenomenon. These findings suggest that MC-EXO uptake in HLFs and the release of mast cell exosomal cargo impacts collagen synthesis, bypassing the TGF-β-Smad-transcription axis.

As previous large-scale clinical studies of pharmacologic therapy for IPF have focused predominantly on TGF-β and associated signaling pathways in fibroblast proliferation and activation, the preponderance of clinical trial evidence to date suggests that pharmacologic therapy for IPF is only partially beneficial. A notable absence of information exists about the exact mechanisms of action of these therapies. The results disclosed herein show that other pathways, like the transcellular exchange of MC-EXO cargo to HLFs, exist that can trigger collagen synthesis in the ER bypassing transcription of fibrillar genes (FIG. 18C). The intracellular events of collagen synthesis within the ER consist of post-translational modification of proline residues in newly synthesized collagenous polypeptide chains. This essential proline hydroxylation reaction is catalyzed by the rate limiting enzyme collagen prolyl 4-hydroxylase (C-P4H).

Figure 4:
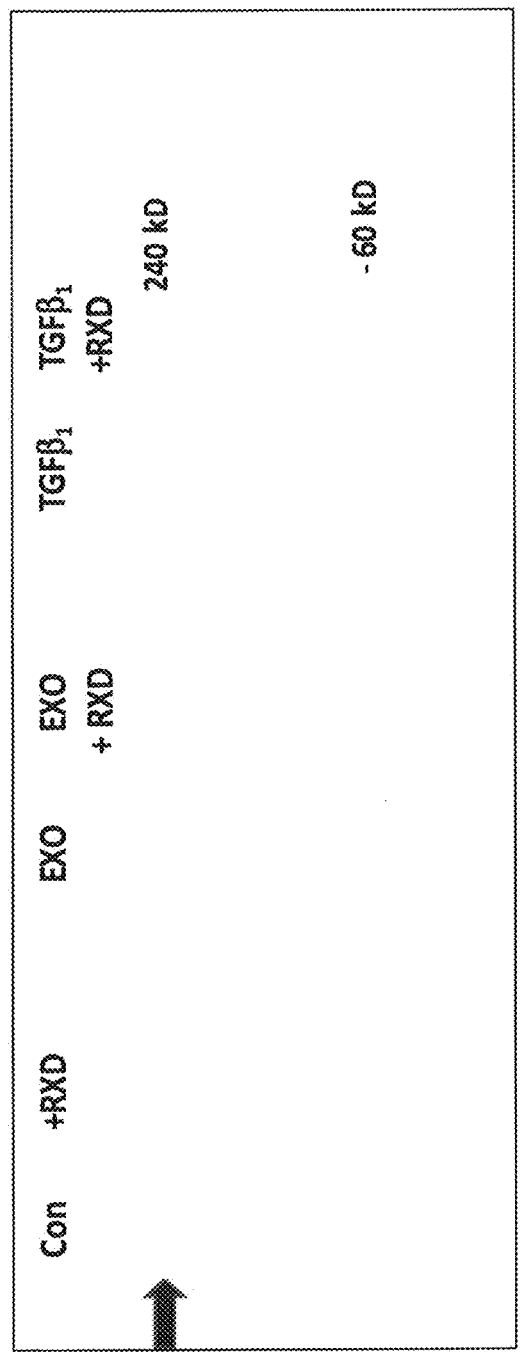
FIG. 4. RXD decreases the relative expression of c-P4H tetramer, the catalytically active form of collagen P4H. Western blotting on a gradient gel was performed on human lung fibroblast homogenates in non-denaturing conditions and probed with anti-α-subunit monomer (60 kD). Tetramer is found at 240 kD at arrow. RXD increased the α-subunit monomer abundance in all cases (60 kD band). RXD was used at 10 mg/ml.

Example 5: RXD Decreases the Relative Expression of c-P4H Tetramer, the Catalytically Active Form of Collagen P4H, the Enzyme Responsible for Prolyl Hydroxylation in the Synthesis of Newly Formed Collagen It is hypothesized that a potential means by which RXD inhibits collagen formation is by decreasing the abundance of catalytically active c-P4H tetramer. The inventors estimated the relative abundance of c-P4H in human lung fibroblasts either alone, co-cultured with mast cell exosomes, or with the addition of exogenous TGF-β±RXD by Western blot probing for the c-P4H α-subunit (FIG. 4).

It was observed that RXD decreased the relative expression of c-P4H tetramer (at arrow—240 kD) by ~5% (Con versus RXD); ~55% (+exosomes (EXO) versus EXO+RXD); ~75% (+TGF-β versus TGF-β+RXD). These results suggest that one aspect of RXD's action is to interfere with c-P4H tetramer formation thereby interrupting proline hydroxylation of protocollagen and preventing new collagen formation.

Example 6: RXD Acts as a Mast Cell Stabilizer

Figures 5A, 5B:
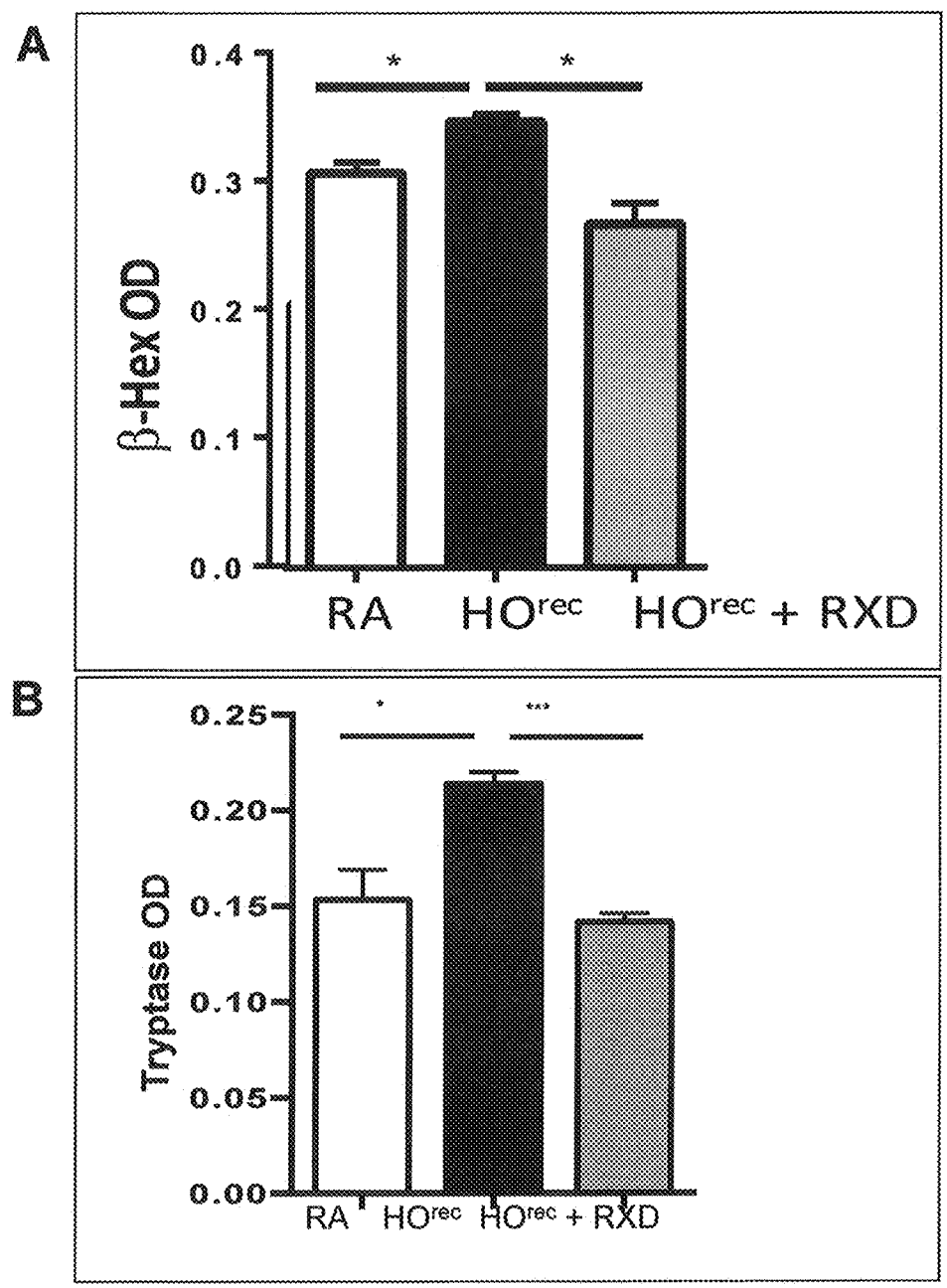
FIG. 5A-5C. RXD decreases mast cell degranulation in vitro in response to oxygen supplementation followed by recovery in room air. A. β-hexosaminadase (β-hex) and B. mast cell tryptase were measured in mast cell supernatants at the 72 h time point in timed controls (room air (RA)), $HO^{rec}$ defined as recovery in 2 days of room air following 1 day in high oxygen and $HO^{rec}$+RXD with addition of PHD inhibitor in the media bathing the cells. RXD was used at 10 mg/ml. *P<0.05,*P<0.001, n=3 experiments. C. The increase in the number of mast cells seen in vivo in pulmonary fibrosis is reduced with RXD in the experimental bleomycin (Bleo) mouse model. *P<0.001, saline versus bleomycin treatment; *P<0.05, bleo vs bleo+RXD. NS=not significant FIG. 6. Cartoon depicting modes of mast cell-dependent activation of fibroblasts (FB).
Figure 5C:
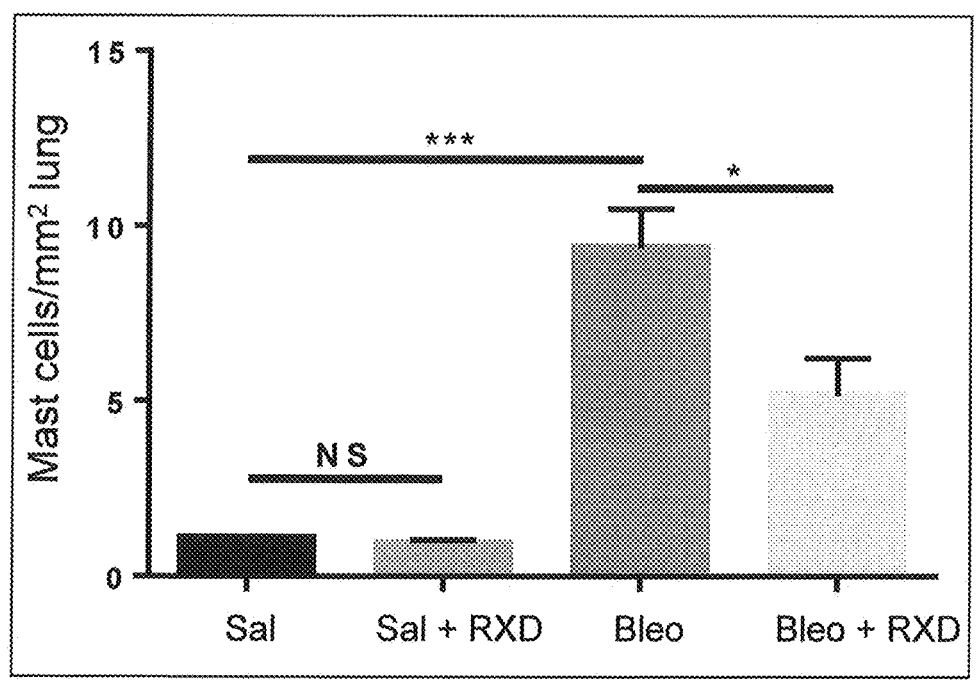

RXD was added to the supernatant bathing mast cells (human mastocytoma cells) after exposure to high oxygen for 24 hours (80%) followed by recovery in room air for 2 days (High oxygen recovery ($HO^{rec}$) and High oxygen recovery+RXD ($HO^{rec}$+RXD)). Mast cell degranulation was assessed by measuring the release of β-hexosaminadase (β-hex), a classic indicator of mast cell degranulation (FIG. 5A) and Tryptase (FIG. 5B). RXD stabilizes the mast cells which can prevent release of potentially harmful mast cell products that can cause lung injury, like fibrogenic tryptase. This protocol was designed to mimic the clinical protocol of giving IPF patients hospitalized with acute exacerbations high oxygen then followed by return to room air.

Example 7: Modes of Mast-Cell-Dependent Activation of Fibroblasts (FB)

Figure 6:
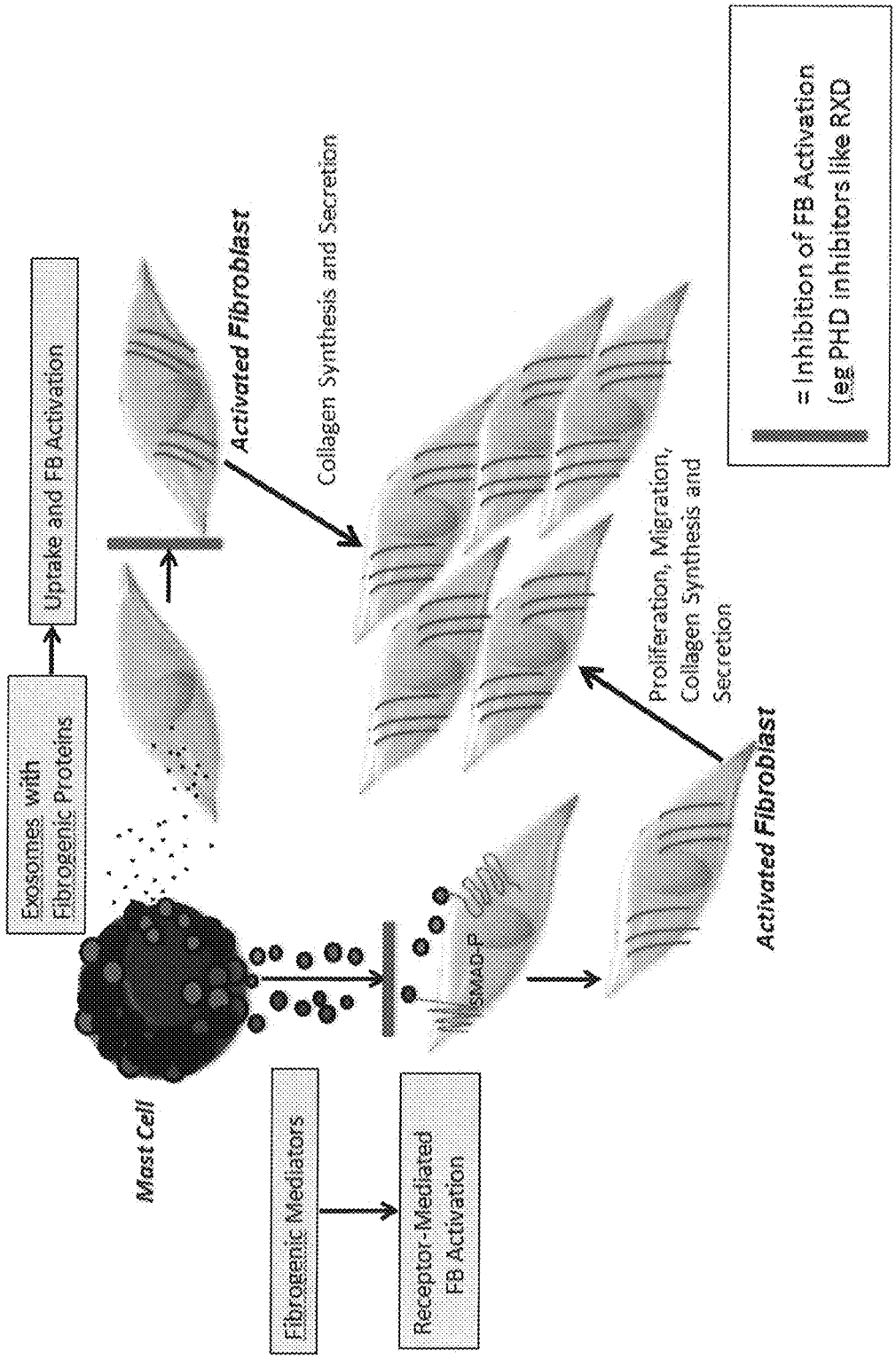
Figure 7:
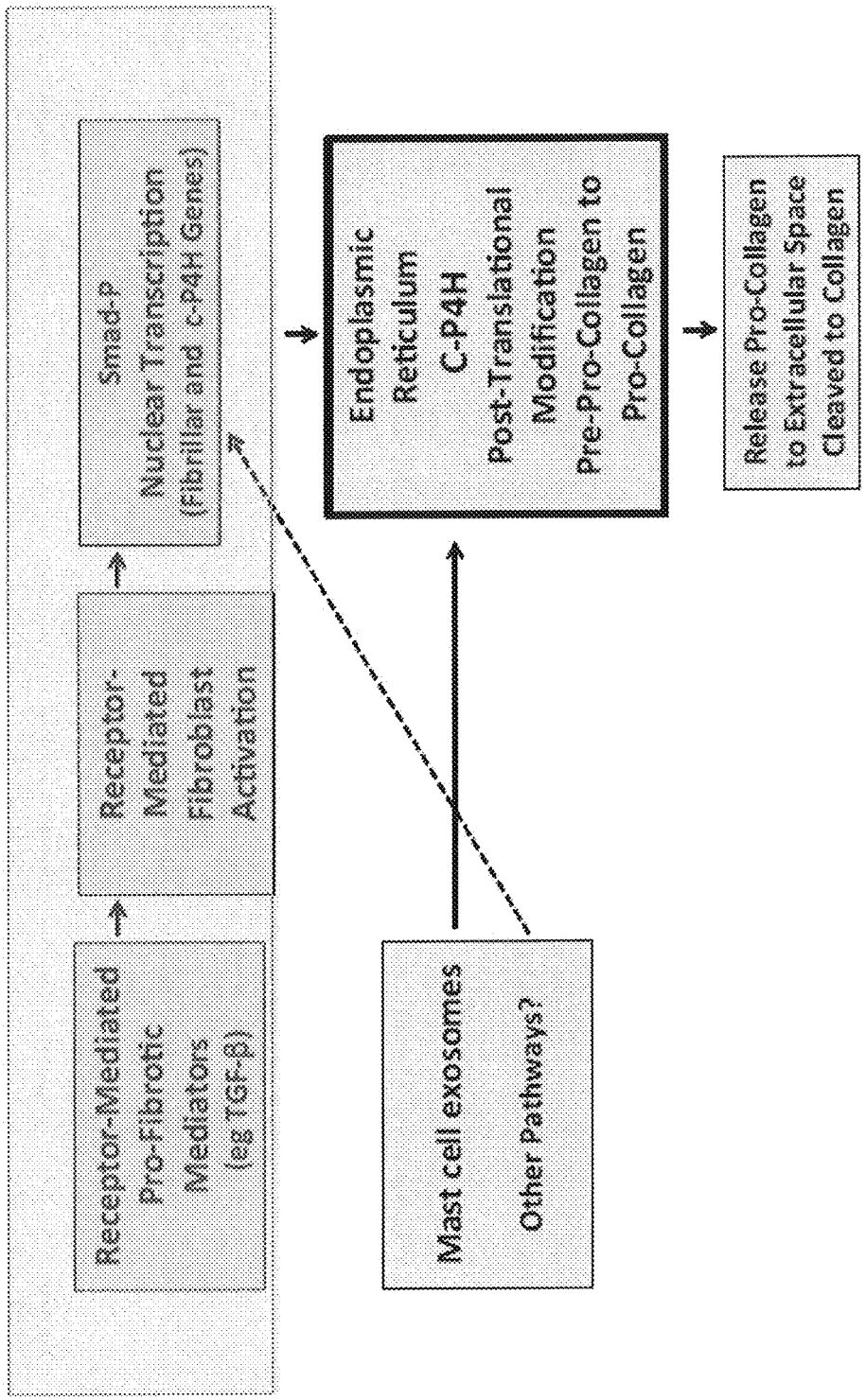
FIG. 7. Diagram of collagen synthesis. This FIG. illustrates the classic ligand-receptor mediated fibrogenic pathway and the additional fibrogenic pathways disclosed in this application. The transforming growth factor beta (TGF-β) pathway is important in virtually all types of fibrosis. These pathways lead to nuclear transcription of fibrillar genes followed by post-translational modification of pre-procollagen in the endoplasmic reticulum (ER). The additional fibrogenic pathways that may bypass nuclear transcription and target the ER directly, include mast cell exosomes demonstrated in this application. Post-translational modification of pre-pro-collagen by c-P4H is the rate-limiting step in producing pro-collagen, the precursor of collagen.
Figures 8A, 8B, 8C:
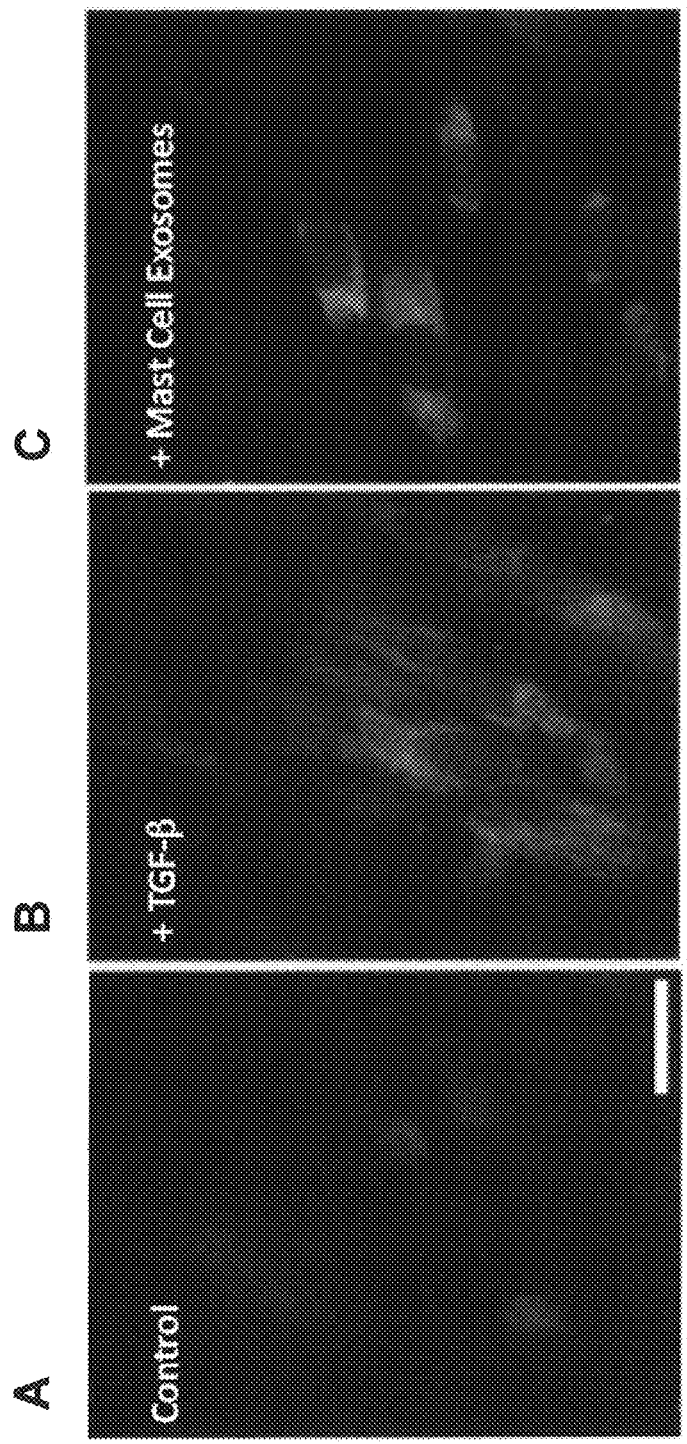
FIG. 8A-8C. Stimulating human fibroblasts increases C-P4H abundance. Immunoexpression of P4H, a key enzyme in collagen synthesis, in human fibroblasts as shown in A. untreated, B. +TGF-β, and C. +mast cell exosomes (EXO). Nuclei (blue) stained with DAPI. Scale bar=10 μm.
Figure 9:
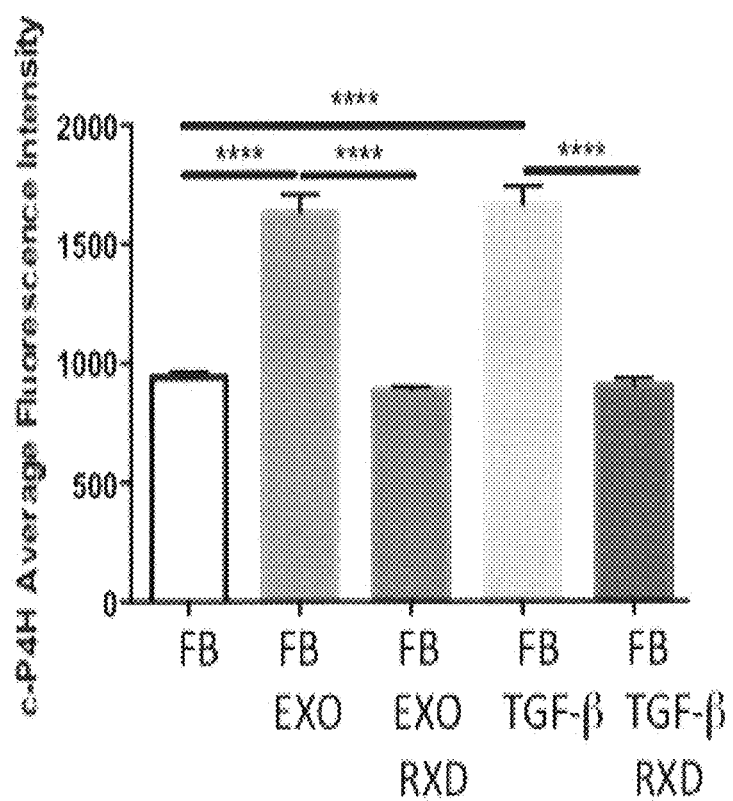
FIG. 9. Roxadustat inhibits the increase in C-P4H in stimulated human fibroblasts. Immunoexpression of prolyl-4-hydroxylase (P4H). The relative acquired pixel intensity of the P4H immunofluorescence (green) was significantly greater in the HLF exposed to TGF-β or mast cell exosomes (EXO) compared to untreated human fibroblasts. ****P<0.001.
Figures 10A, 10B:
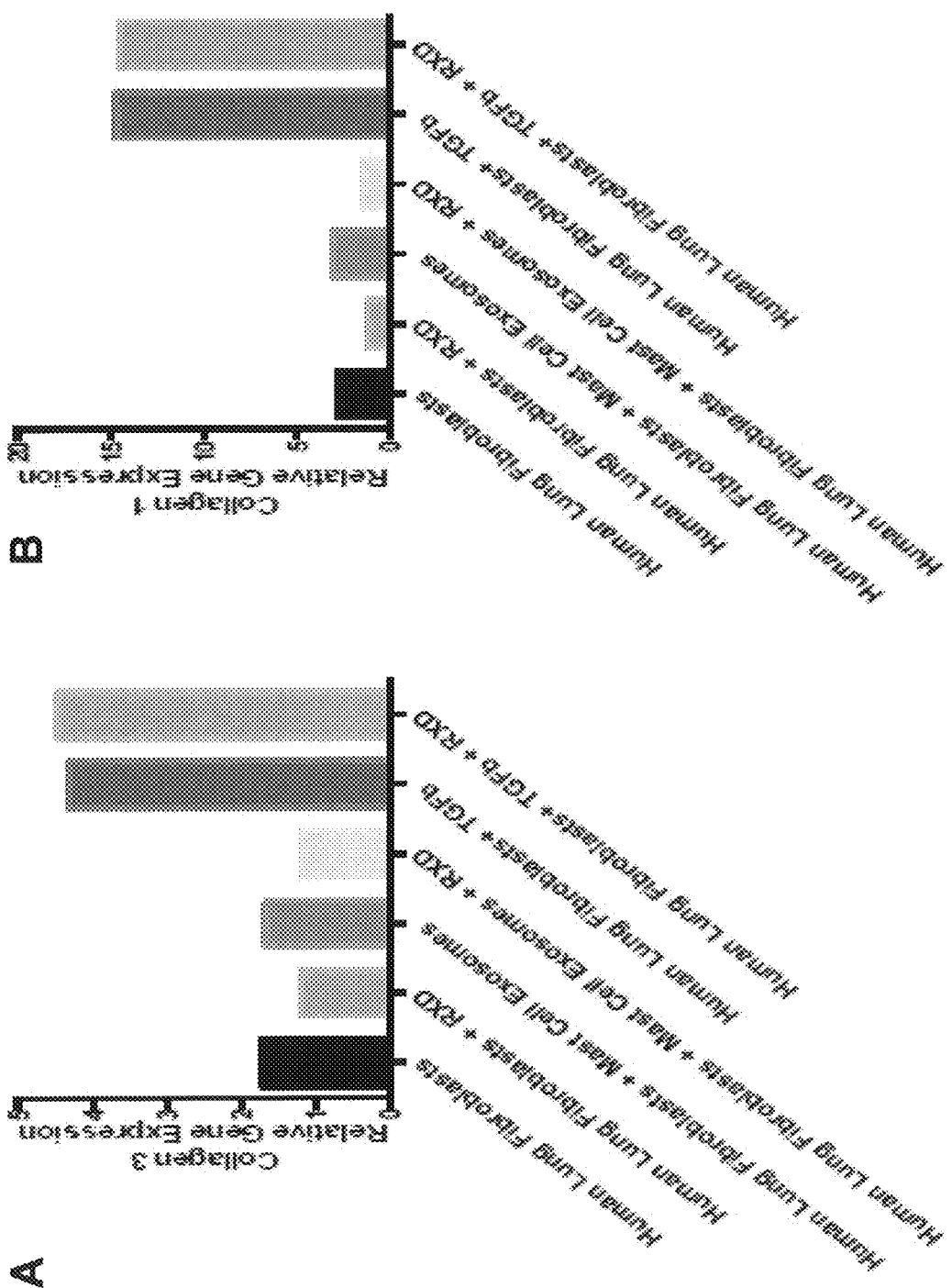
FIG. 10A-10B. Roxadustat (RXD) Has No Effect on Fibroblast Collagen Gene Transcripts. HiF Prolyl hydroxylase domain inhibitors like roxadusat act at the level of post-translational modification and not at the transcriptional level. Therefore roxadusat did not alter the increase in fibrillar gene transcripts as occurs with TGF-β inhibition. A. Collagen 3 relative gene expression under recited conditions. B. Collagen 1 relative gene expression under recited conditions.
Figures 11A, 11B:
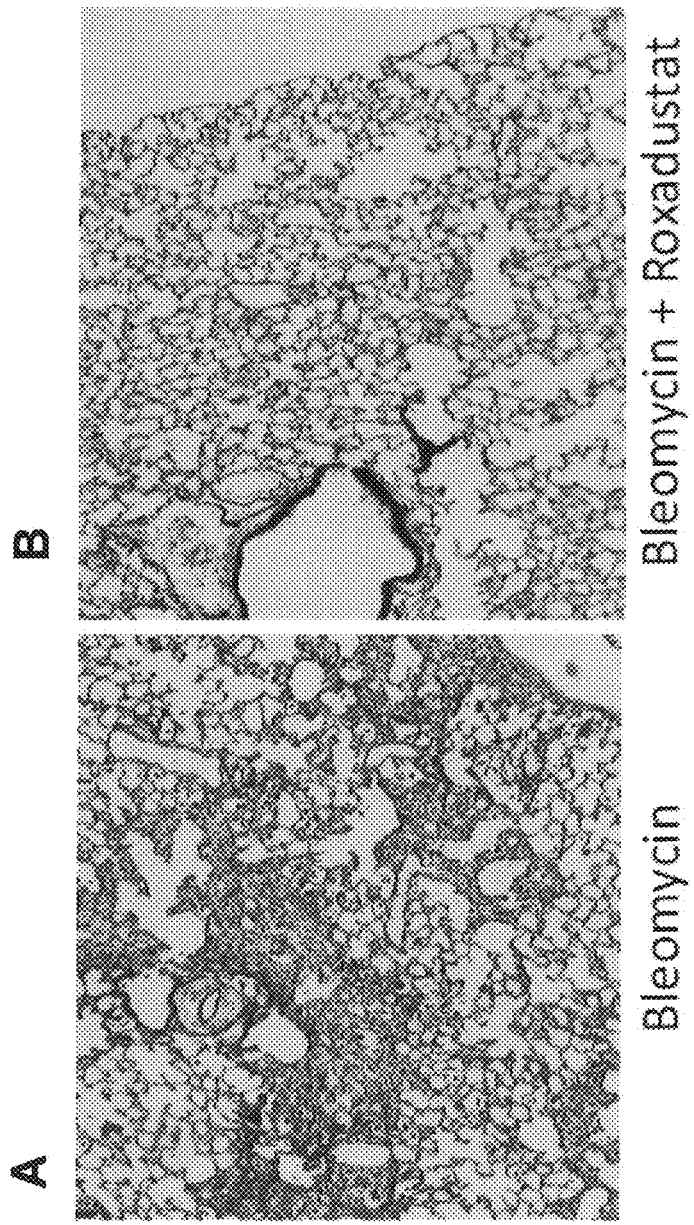
FIG. 11A-11B. In Vivo Murine Model of pulmonary fibrosis. Bleomycin-induced pulmonary fibrosis is reduced with roxadustat treatment. Representative micrographs of Masson's trichrome-stained lungs from bleomycin-treated mice from the 14 d time point. Roxadustat decreased the fibrosis.
Figure 12:
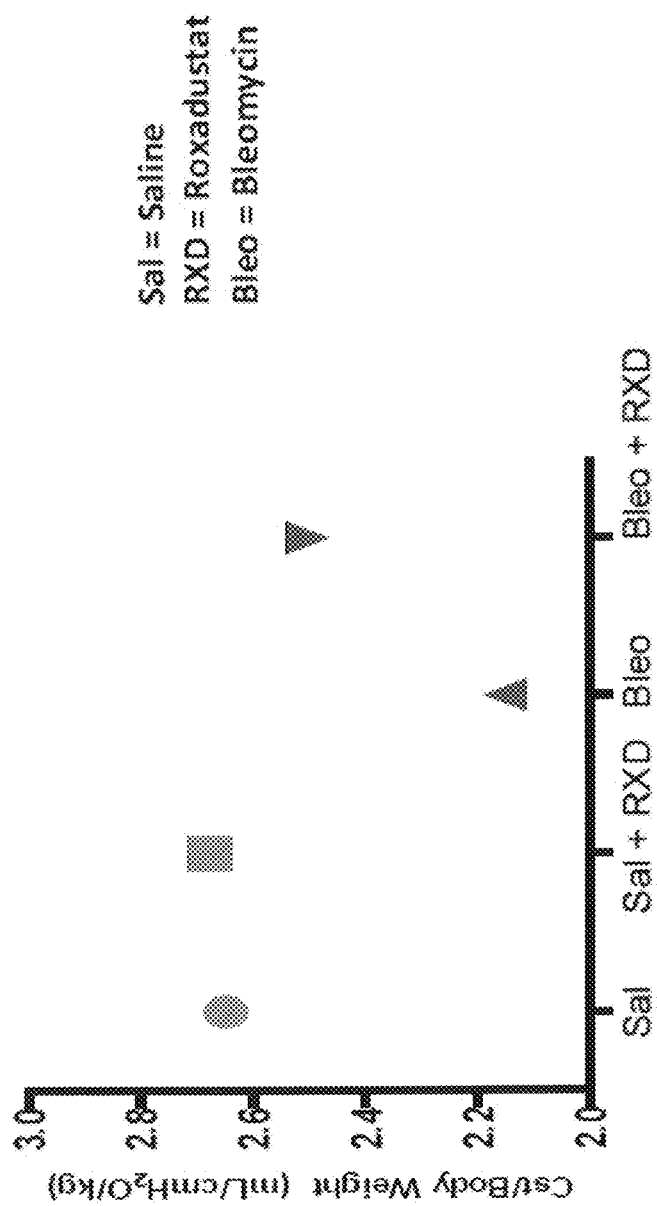
FIG. 12. Roxadustat normalizes the bleomycin-induced decrease in lung compliance. Pulmonary function tests demonstrate that treatment with roxadustat (RXD) diminishes the decreased lung compliance associated with bleomycin (Bleo). Sal=Saline vehicle.
Figures 13A, 13B:
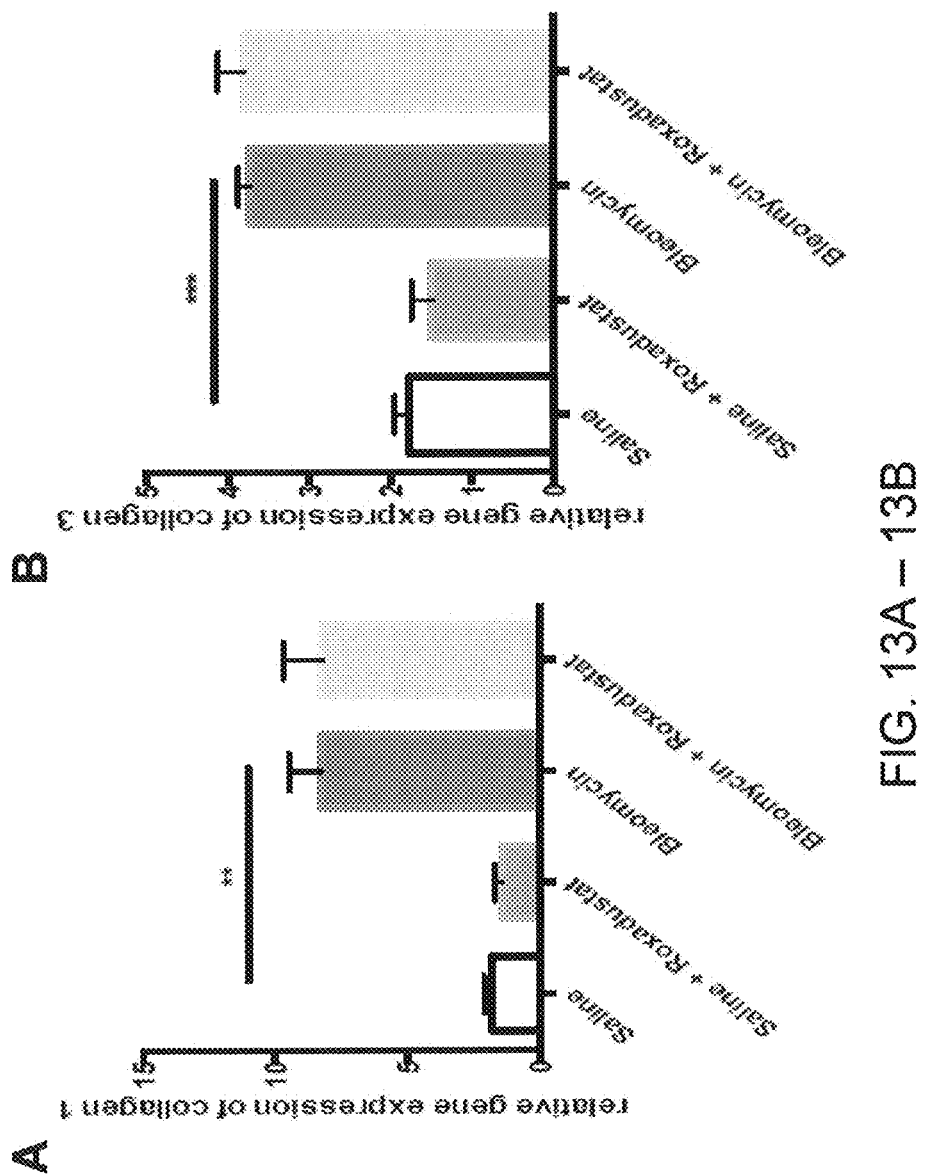
FIG. 13A-13B. Roxadustat (RXD) Has No Effect on Lung Collagen Gene Transcripts. Roxadusat did not alter the increase in fibrillar gene transcripts resulting from exposing the lung to bleomycin. A. Collagen 1 relative gene expression under recited conditions. B. Collagen 3 relative gene expression under recited conditions.
Figure 14:
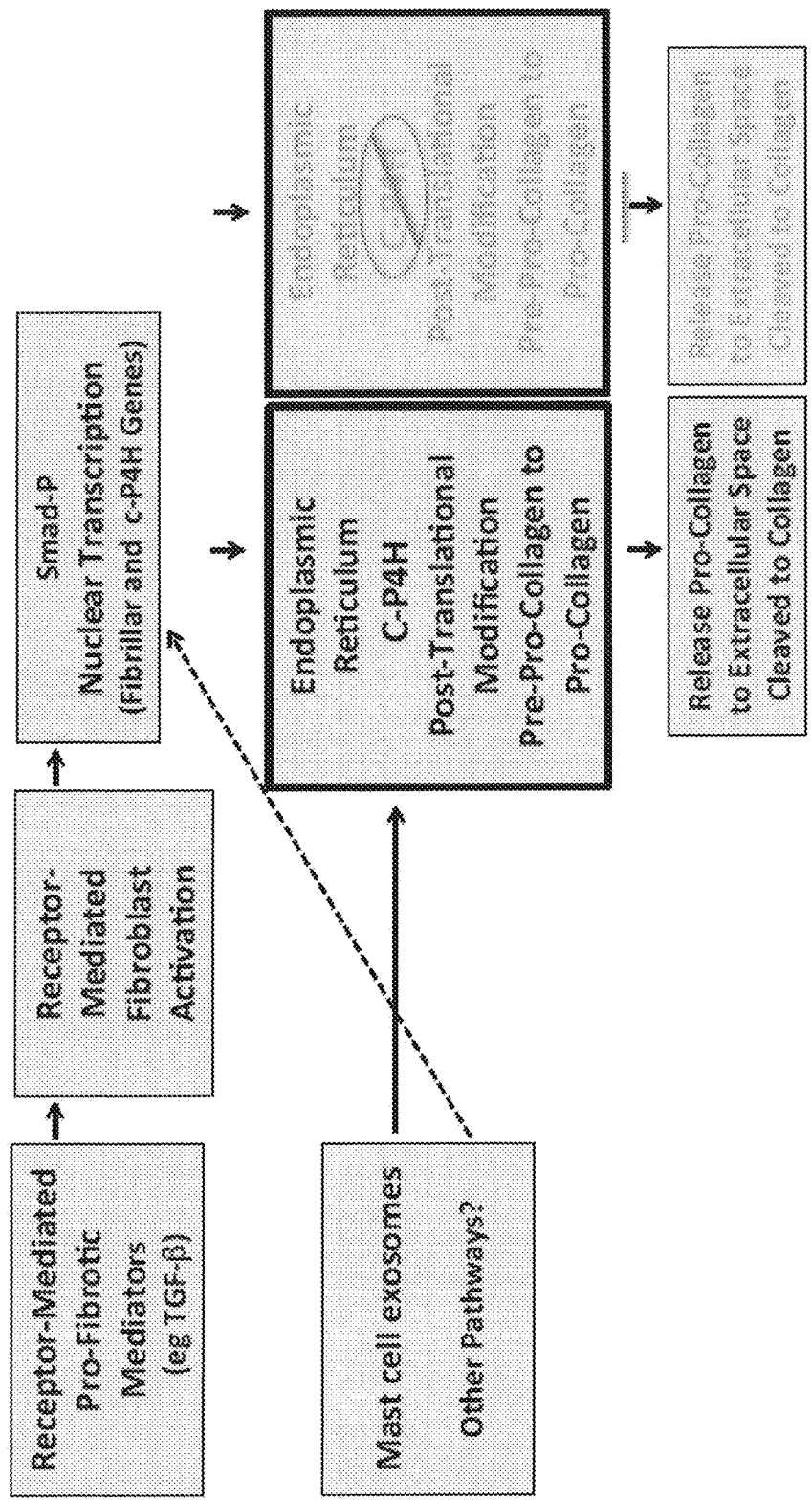
FIG. 14. Diagram of C-P4H as a Druggable Target of Collagen Synthesis. Using a HIF PHD inhibitor like roxadusat interrupts the post-translational modification of pre-pro-collagen in the ER by preventing hydroxylation of pralines in the pre-pro-collagen peptide. Insufficiently hydroxylated chains do not form triple-helical domains that are stable at body temperature and therefore undergo degradation.
Figures 15A, 15B, 15C, 15D:
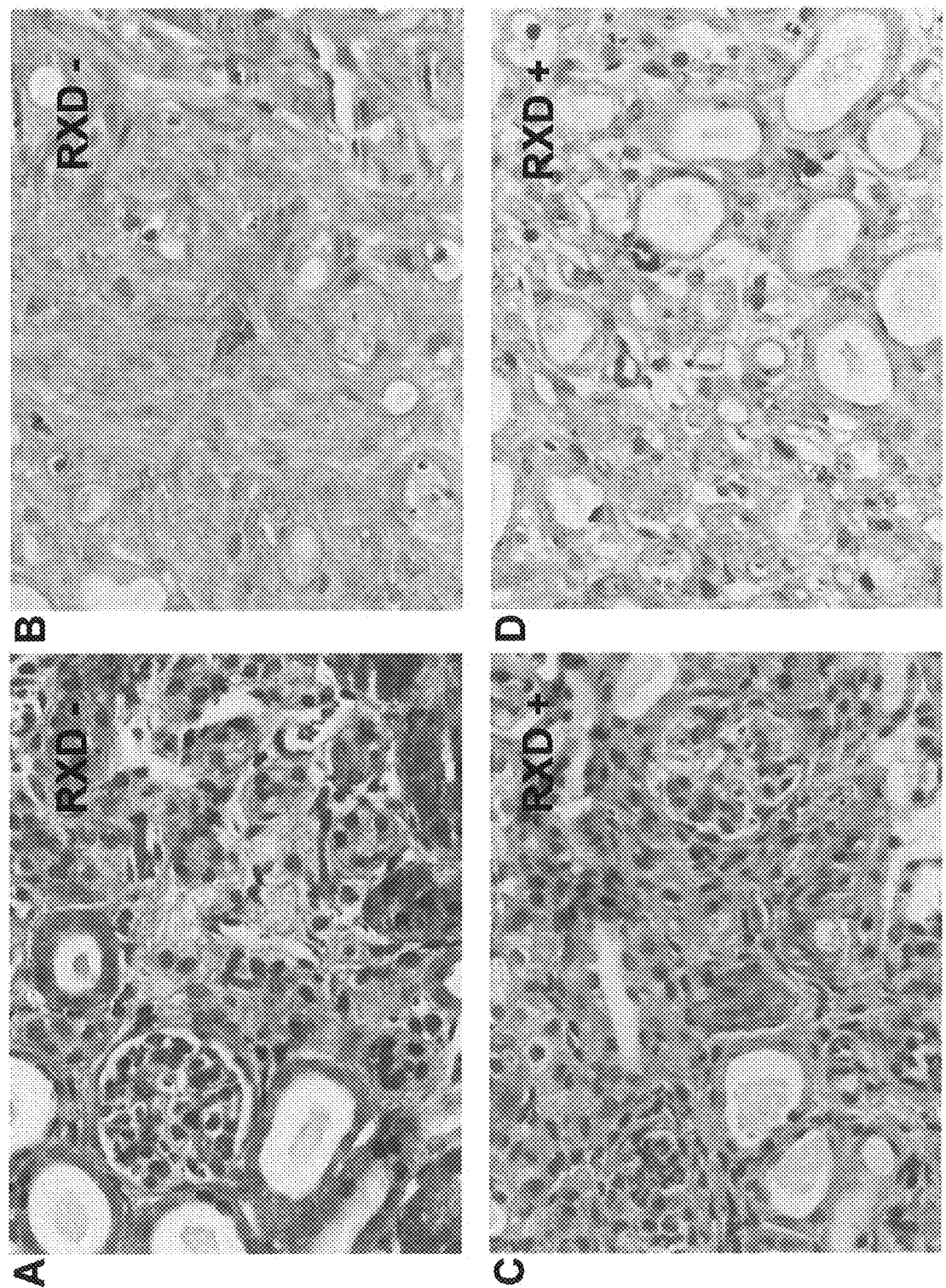
FIG. 15A-15D. Roxadustat and kidney unilateral ureteral obstruction (UUO). All kidney sections were stained with Masson's Trichrome. A. Stained cortex of untreated kidneys (RXD−) on Day 14 of unilateral ureteral obstruction. B. Stained medulla of untreated kidneys (RXD−) on Day 14 of unilateral ureteral obstruction. C. Stained cortex of kidneys treated with roxadustat (RXD+) on Day 14 of unilateral ureteral obstruction. D. Stained medulla of kidneys treated with roxadustat (RXD+) on Day 14 of unilateral ureteral obstruction.

FIG. 6 shows the contributions of mast cells to fibroblast collagen synthesis and secretion. Left arm of the figure shows how pro-fibrogenic mast cell mediators like histamine, tryptase, renin/ANG II, TGF-β, for example, activate FBs via receptor activation and SMAD signaling pathways. Receptor-mediated activation of FBs leads to their proliferation, migration, and activation of collagen synthesis and secretion. The other arm represents the novel pathway disclosed in this application and shows that mast cell exosomes, which contain profibrotic proteins, are taken up by neighboring FBs, and are capable of stimulating collagen synthesis and secretion via a non-SMAD pathway. The receptor-mediated and exosomal pathways in FB activation are blocked with HIF PHD inhibitors, like RXD (red bar).

Figures 20A, 20B, 20C, 20D, 20E:
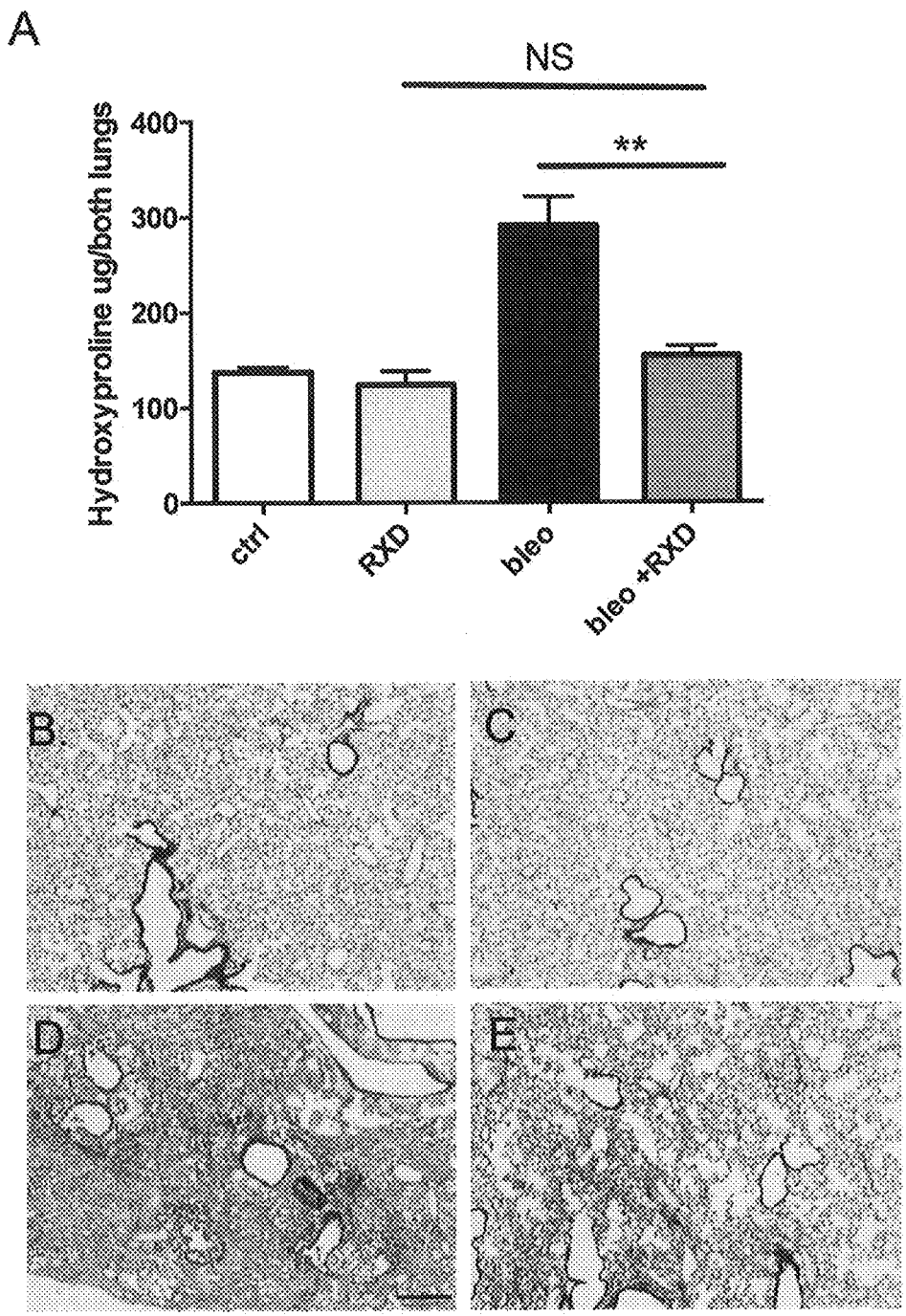
FIG. 20A-20E. RXD inhibits bleomycin-induced fibrosis in the murine lung. A. Lung hydroxyproline content is significantly reduced in RXD-treated bleomycin mice. B.-E. Masson's trichrome stained lung sections for collagen deposition: B=Saline instilled control mouse, C=RXD-treated saline instilled control mouse, D=Bleomycin-instilled mouse, E=RXD+Bleomycin-instilled mouse. **P<0.01, Bleo versus Bleo+RXD. NS=not significant. N=5 mice/group. Scale bar=250 µm.

Example 8: Effects of RXD in the Bleomycin Experimental Model of Pulmonary Fibrosis 8-week old mice (C57BL/6J) were used to address whether RXD inhibits the development of bleomycin-induced pulmonary fibrosis. A single oropharyngeal administration of bleomycin was followed by therapeutic delivery of RXD (10 mg/kg) on days 7, 9, 11, 13, 15, 17, and 19 representing the periods of fibroproliferation and established fibrosis. Mice were sacrificed on day 21. Bleomycin caused an increase in lung hydroxyproline content that was significantly decreased with RXD (FIG. 20A). Histological assessment in Masson's trichrome stained lungs showed that RXD lessened the severity of fibrosis due to bleomycin (compare FIG. 20E versus FIG. 20D).

Example 9: Treatment with RXD Decreases Renal Fibrosis in UUO. In Vivo Unilateral Ureteral Obstruction (UUO) Model All animal treatments and experiments were approved by the Institutional Animal Care and Use Committee of Weill Cornell Medical College. Mice were anesthetized intraperitoneally with a cocktail of ketamine (90 mg/kg) and xylazine (4 mg/kg). Mice C57BL/6J underwent right unilateral ureteral ligation with 4-0 silk suture through an abdominal midline incision under sterile conditions. Sham-operated control (CON) animals underwent identical operations, however, with manipulation of the right ureter only. Delivery of Roxadustat (10 mg/kg) on days 0, 2, 4, 6, 8, was administered IP. Mice were sacrificed on Day 14.

Kidneys were harvested and fixed in 10% neutral buffered formalin followed by embedding in paraffin. Sections (5 um) were collected and Masson's trichrome staining was performed using a kit (Richard-Allen Scientific) to detect collagen (blue stain). Slides of paraffinized tissue sections were deparaffinized, rehydrated, and washed in distilled water. Sections were subsequently stained using components from the trichrome kit and according to the manufacturer's protocol. After dehydrating and clearing in xylene, the sections were mounted with coverslips in Vectamount (Vector Laboratories). Tissue sections were examined with an inverted epifluorescence microscope (Nikon Eclipse TE 2000-U) interfaced to a SPOT Insight 2 megapixel color camera (Diagnostic Instruments).

Results

Figures 16A, 16B, 16C, 16D, 16E, 16F:
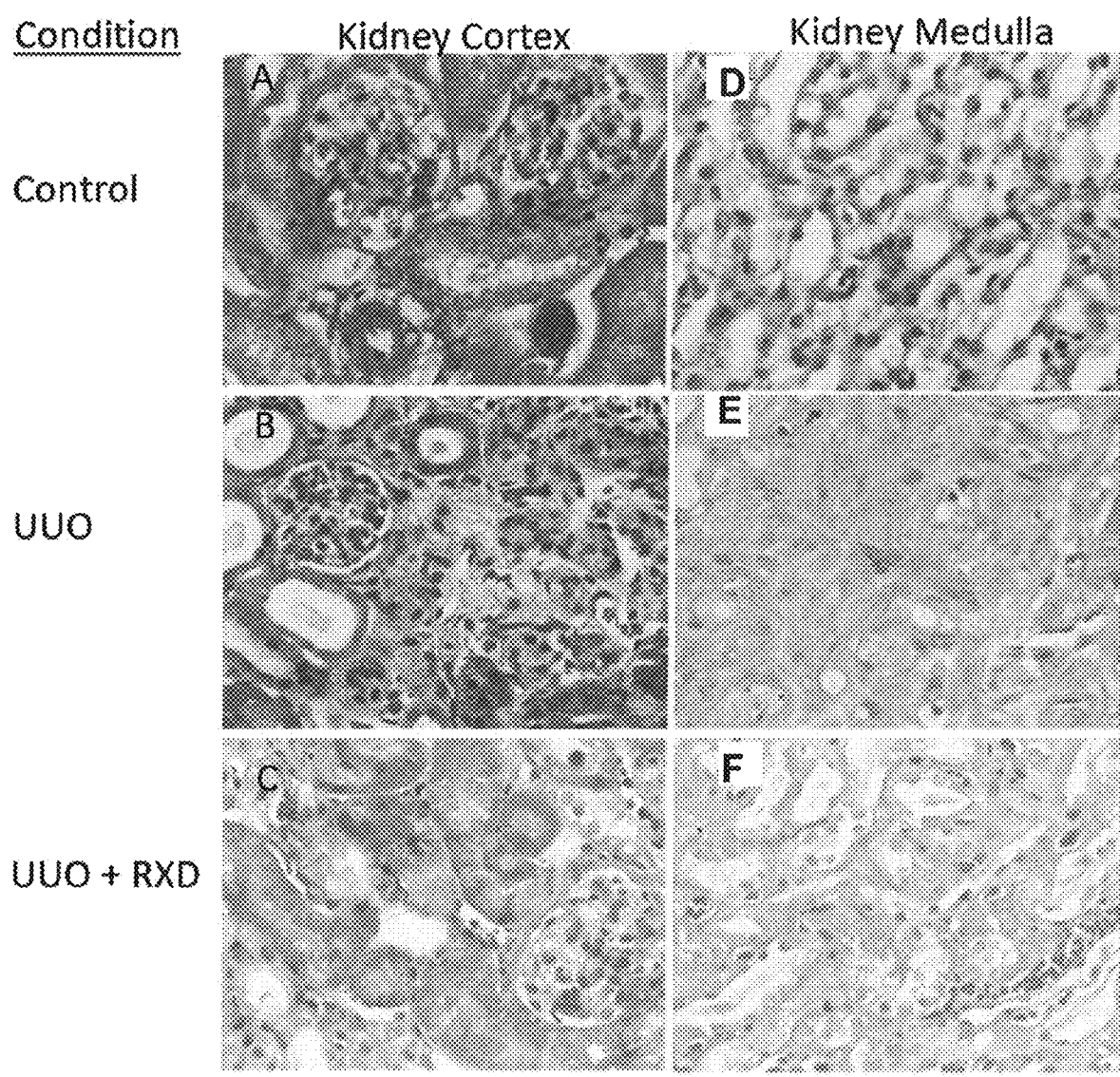
FIG. 16A-16F. Treatment with RXD decreases renal fibrosis in UUO. Representative paired cortical and medullary sections (from the same kidney) of control, UUO, and UUO+RXD kidneys stained with Masson's Trichrome. Collagen is stained blue. A. Collagen staining of control kidney cortex. B. Collagen staining of UUO kidney cortex. C. Collagen staining of UUO kidney medulla treated with RXD. D. Collagen staining of control kidney medulla. E. Collagen staining of UUO kidney medulla. F. Collagen staining of UUO kidney medulla treated with RXD. Collagen staining was abundant in the UUO kidney (cortex and medulla)(B and E), compared to control kidney sections (A and D). Treatment with RXD lessened the fibrosis as seen in UUO kidney cortex and medulla (C and F).

Treatment with RXD decreases renal fibrosis in UUO. Collagen staining (blue) was abundant in the UUO kidney (cortex and medulla) (FIGS. 15A, 15B, 16B and 16E), compared to control kidney sections (FIGS. 16A and 16D). Treatment with RXD lessened the fibrosis as seen in UUO kidney cortex and medulla (FIGS. 15C, 15D, 16C and 16F).

Figure 17:
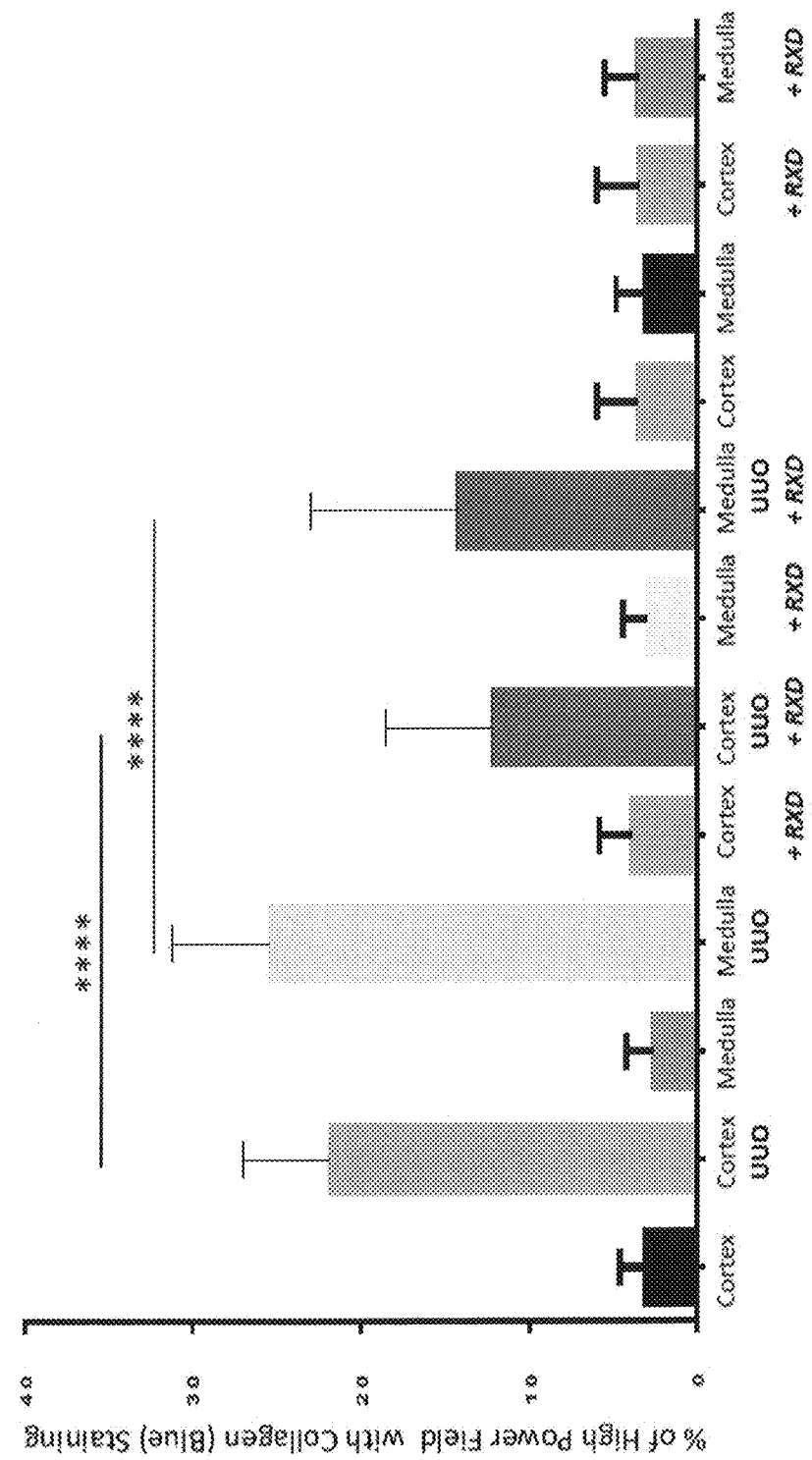
FIG. 17. RXD Reduces Fibrosis in UUO Kidney. Collagen (blue) staining was quantified in the Masson's Trichrome stained fixed kidney sections pixel by pixel in multiple high powered fields. ****P<0.0001 between Cortex UUO and Cortex UUO+RXD; and Medulla UUO and Medulla UUO+RXD. There was no significant difference between control cortex and medulla collagen staining with and without RXD. N=4 mice/group.

In addition, collagen (blue) staining was quantified in the Masson's Trichrome stained fixed kidney sections pixel by pixel in multiple high powered fields. ****$P<0.0001$ between Cortex UUO and Cortex UUO+RXD; and Medulla UUO and Medulla UUO+RXD. There was no significant difference between control cortex and medulla collagen staining with and without RXD. N=4 mice/group. See FIG. 17.

What is claimed is:

1. A method of treating fibrosis of an organ in a patient in need of such treatment, comprising administering to the patient an effective amount of a collagen prolyl-4-hydroxylase (c-P4H) inhibitor, wherein the organ is lung or kidney, wherein the inhibitor of c-P4H is a propyl hydroxylase domain (PHD) inhibitor, and wherein the PHD inhibitor is
   (i) selected from the group consisting of Roxadustat (RXD) (FG-4592), Vadadustat (AKB-6548), Daprodustat (GSK1278863), and Molidustat (BAY85-3934); or
   (ii) has the following chemical structure

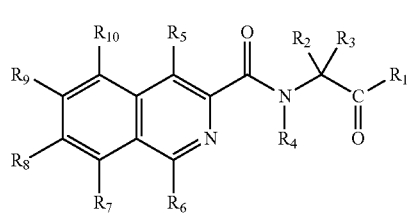

(I)

wherein:
R1 is selected from the group consisting of hydroxyl, alkoxy, substituted alkoxy, aryloxy, and substituted aryloxy;

R2 and R3 are independently selected from the group consisting of hydrogen, alkyl, substituted alkyl, cycloalkyl, substituted cycloalkyl, aryl, substituted aryl, heterocycloalkyl, substituted heterocycloalkyl, heteroaryl, and substituted heteroaryl; or R2 and R3 together with the carbon atom to which they are attached form a cycloalkyl, substituted cycloalkyl, heterocycloalkyl, or substituted heterocycloalkyl;

R4 is selected from the group consisting of hydrogen, alkyl, and substituted alkyl;

R5 is selected from the group consisting of hydroxyl, alkoxy, and substituted alkoxy;

R6 is selected from the group consisting of hydrogen, alkyl, substituted alkyl, cycloalkyl, substituted cycloalkyl, cyano, halo, hydroxyl, alkoxy, substituted alkoxy, amino, substituted amino, aminoacyl, substituted aminoacyl, cycloalkoxy, substituted cycloalkoxy, aryl, substituted aryl, aryloxy, substituted aryloxy, heterocycloalkyl, substituted heterocycloalkyl, heteroaryloxy, substituted heteroaryloxy, heteroaryl, and substituted heteroaryl; and R7, R8, R9 and R10 are independently selected from the group consisting of hydrogen, halo, alkyl, substituted alkyl, cycloalkyl, substituted cycloalkyl, aryl, substituted aryl, heteroaryl, substituted heteroaryl, alkoxy, substituted alkoxy, and substituted aryloxy.

2. The method of claim 1, wherein the c-P4H inhibitor is administered intermittently.

3. The method of claim 2, wherein the c-P4H inhibitor is administered every other day, every three days, every five days or once a week.

4. The method of claim 2, wherein the c-P4H inhibitor is administered every hour, every two hours, every three hours, every six hours or every twelve hours.

5. The method of claim 1, wherein the c-P4H inhibitor is administered by intravenous (i.v.) injection, intraperitoneal (i.p.) injection, subcutaneous (s.c.) injection, or aerosolized delivery.

6. The method of claim 1, wherein the PHD inhibitor specifically inhibits the activity of c-P4H.

7. The method of claim 1, wherein R6 is alkyl.

8. The method of claim 7, wherein said alkyl is methyl.

9. The method of claim 1, wherein R5 is hydroxyl.

10. The method of claim 1, wherein R8 is aryloxy.

11. The method of claim 1, wherein R6 is methyl and R5 is hydroxyl.

12. The method of claim 1 wherein said PHD inhibitor is FG-4592, wherein said FG-4592 has the chemical name N-[(4-hydroxy-1-methyl-7-phenoxyisoquinolin-3-yl)carbonyl)glycine)] and the following chemical structure:

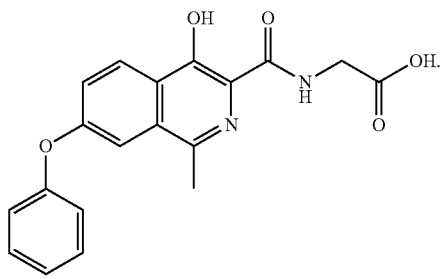

Roxadustat (FG-4592)

13. The method of claim 1 wherein the PHD inhibitor is administered in an amount between 0.2 mg/kg and 20 mg/kg.

14. The method of claim 1 wherein the PHD inhibitor is administered at an amount between 50 mg/kg and 200 mg/kg.

15. A method of treating fibrosis of an organ in a patient in need of such treatment, comprising administering to the patient an effective amount of a pharmaceutical composition that inhibits the activity of collagen prolyl-4-hydroxylase (c-P4H), wherein the inhibition of the activity of the c-P4H enzyme is achieved by a method selected from the group consisting of introducing a nucleic acid inhibitor, the CRISPR/Cas system, the Cre/Lox system, the TALEN system, and homologous recombination, wherein the nucleic acid inhibitor is selected from the group consisting of an antisense RNA, a small interfering RNA, an RNAi microRNA, an artificial microRNA, and a ribozyme, and wherein the organ is kidney or lung.

* * * * *